(12) United States Patent
Caluori

(10) Patent No.: US 9,402,985 B2
(45) Date of Patent: Aug. 2, 2016

(54) SELF-CLEANING SUCTION DEVICE

(71) Applicant: Michael Caluori, Missoula, MT (US)

(72) Inventor: Michael Caluori, Missoula, MT (US)

( * ) Notice: Subject to any disclaimer, the term of this patent is extended or adjusted under 35 U.S.C. 154(b) by 18 days.

(21) Appl. No.: 13/946,930

(22) Filed: Jul. 19, 2013

(65) Prior Publication Data

US 2013/0299019 A1 Nov. 14, 2013

Related U.S. Application Data

(62) Division of application No. 12/945,349, filed on Nov. 12, 2010, now Pat. No. 8,518,017.

(60) Provisional application No. 60/260,530, filed on Nov. 12, 2009.

(51) Int. Cl.

| A61M 31/00 | (2006.01) |
|---|---|
| A61M 39/00 | (2006.01) |
| A61C 1/00 | (2006.01) |
| A61C 17/06 | (2006.01) |
| F16L 9/19 | (2006.01) |
| A61M 37/00 | (2006.01) |
| A61M 29/00 | (2006.01) |
| A61M 5/32 | (2006.01) |
| A61M 5/14 | (2006.01) |
| A61M 1/00 | (2006.01) |

(52) U.S. Cl.
CPC .............. A61M 39/00 (2013.01); A61C 1/0076 (2013.01); A61C 17/04 (2013.01); F16L 9/19 (2013.01); *Y10T 137/8593* (2015.04); *Y10T 137/85978* (2015.04)

(58) Field of Classification Search
CPC ..... A61M 31/00; A61M 37/00; A61M 29/00; A61M 5/32; A61M 5/14; A61M 1/00; A61M 27/00; A61B 18/04
USPC ......................................... 604/540, 541, 544
See application file for complete search history.

(56) References Cited

U.S. PATENT DOCUMENTS

| 2,756,740 A | * | 7/1956 | Deane ............................ 604/77 |
| 3,527,219 A | | 9/1970 | Greenberg |
| 4,966,580 A | | 10/1990 | Turner et al. |

(Continued)

FOREIGN PATENT DOCUMENTS

KR    10-2002-0038662 A    5/2002

*Primary Examiner* — Tatyana Zalukaeva
*Assistant Examiner* — Ilya Treyger
(74) *Attorney, Agent, or Firm* — Jean Kyle

(57) ABSTRACT

A self-cleaning suction device has a user's suction end that self-sanitizes externally and internally before and after use, as well as self-sanitizes internally during use. A cover opens to reveal the user's suction end within a containment unit. As the cover opens, the suction end travels from a lower chamber, proceeds through a middle chamber of a sanitizing agent, and is presented for use. After suction is complete, the suction end retracts through an upper chamber with, a scraping feature that removes debris from the outer surface of the mouthpiece, and proceeds down through the middle chamber of a sanitizing agent and a scraping feature that removes debris and the sanitizing agent from the outer surface of the user's suction end. Upon the sealing closure of the cover, the upper and middle chambers are flushed with a sanitizing agent, which is suctioned away along with any collected debris. The user's suction end resides within a lower chamber and can be decontaminated by a UV-C light entering into the lower chamber and/or corresponding chambers. The suction device can also include a liquid-hydration delivery system.

9 Claims, 17 Drawing Sheets

(56) References Cited

U.S. PATENT DOCUMENTS

| | | |
|---|---|---|
| 5,104,315 A | 4/1992 | McKinley |
| 5,365,624 A | 11/1994 | Berns |
| 5,484,405 A * | 1/1996 | Edstrom, Sr. .................. 604/77 |
| 5,980,498 A | 11/1999 | Brown |
| 5,984,145 A | 11/1999 | McAllister |
| 6,152,733 A | 11/2000 | Hegemann et al. |
| 6,314,960 B1 | 11/2001 | Vines |
| 6,358,237 B1 | 3/2002 | Paukovits et al. |
| 6,409,048 B1 | 6/2002 | Belzeski |
| 6,638,236 B2 * | 10/2003 | Thrash et al. ................. 601/160 |
| 6,652,481 B1 | 11/2003 | Brown et al. |
| 6,745,915 B2 * | 6/2004 | Rees ............................ 220/714 |
| 6,851,275 B2 | 2/2005 | Kreutzmann et al. |
| 7,007,502 B2 | 3/2006 | Kreutzmann et al. |
| 7,059,852 B2 | 6/2006 | Chu |
| 7,118,377 B2 | 10/2006 | Inoue et al. |
| 8,281,784 B2 * | 10/2012 | Wachtel .................. 128/203.21 |
| 2004/0045980 A1 | 3/2004 | Robins |
| 2004/0072122 A1 | 4/2004 | Hegemann |
| 2005/0029313 A1 | 2/2005 | Robins et al. |
| 2005/0127103 A1 | 6/2005 | Reid |
| 2005/0187528 A1 | 8/2005 | Berg |
| 2006/0093990 A1 | 5/2006 | Stone et al. |
| 2007/0175469 A1 | 8/2007 | Rohrschneider et al. |
| 2008/0145816 A1 | 6/2008 | Hershey et al. |
| 2009/0198201 A1 | 8/2009 | Adahan |

* cited by examiner

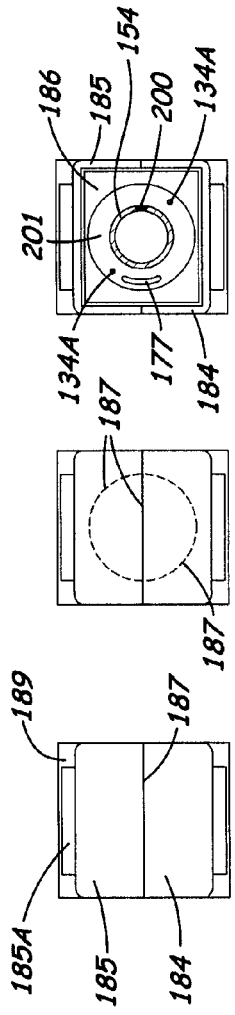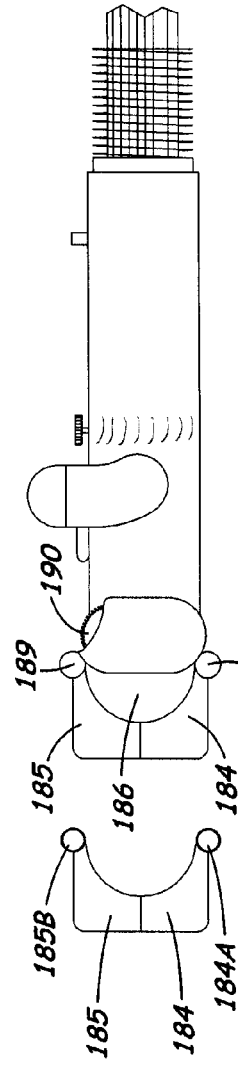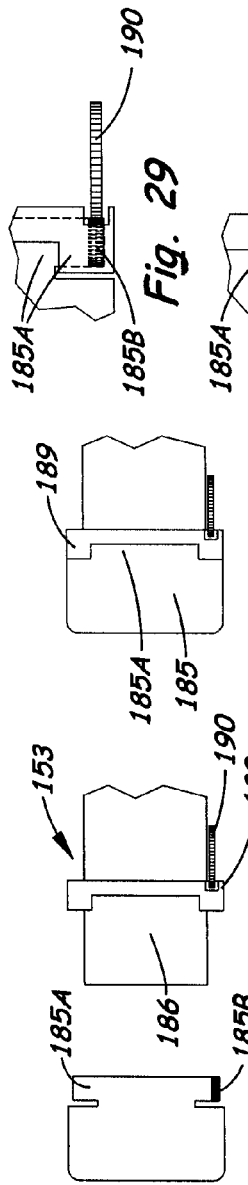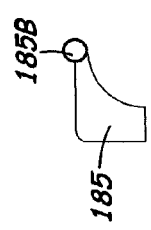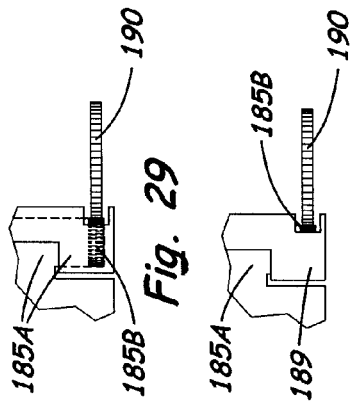

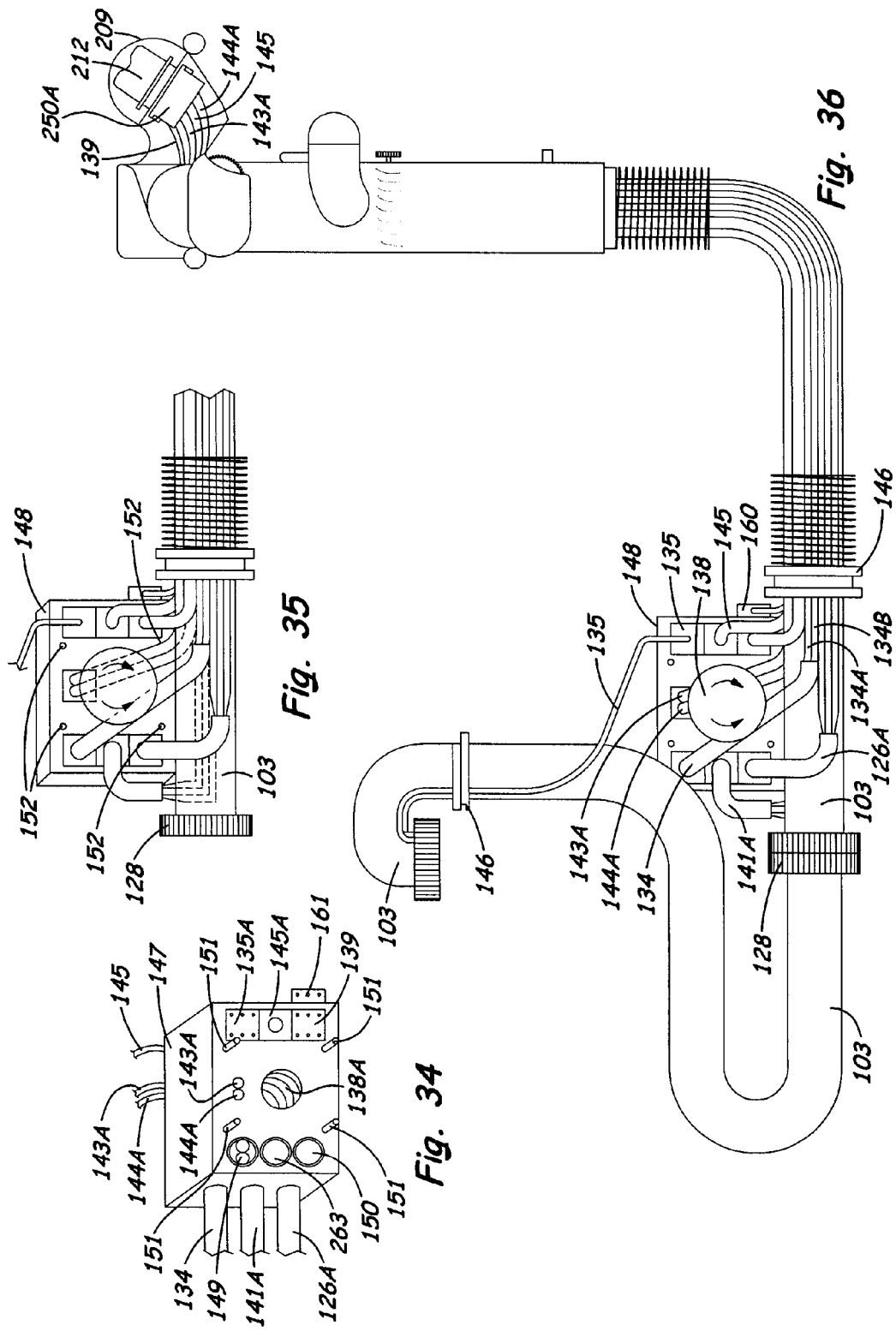

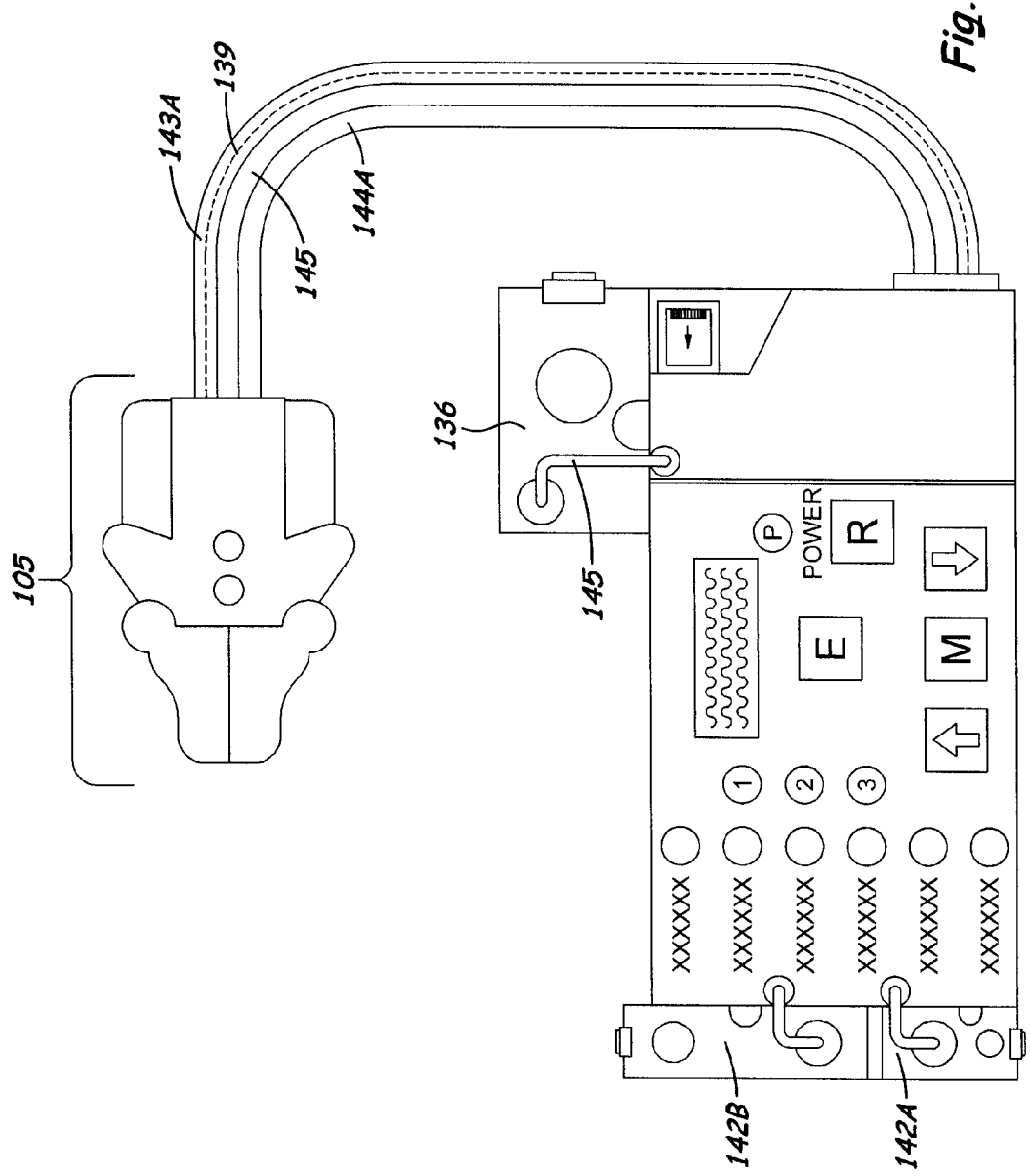

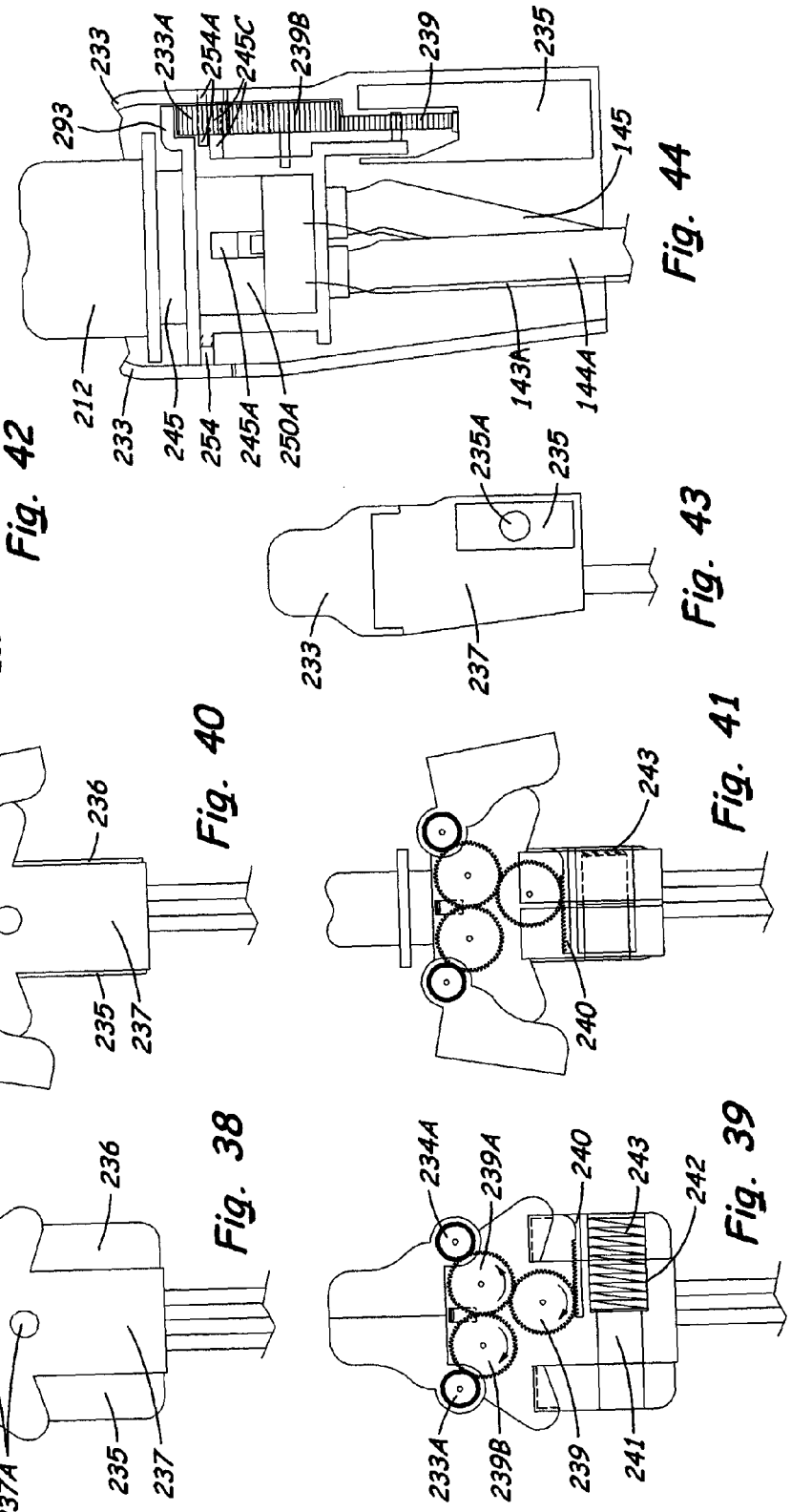

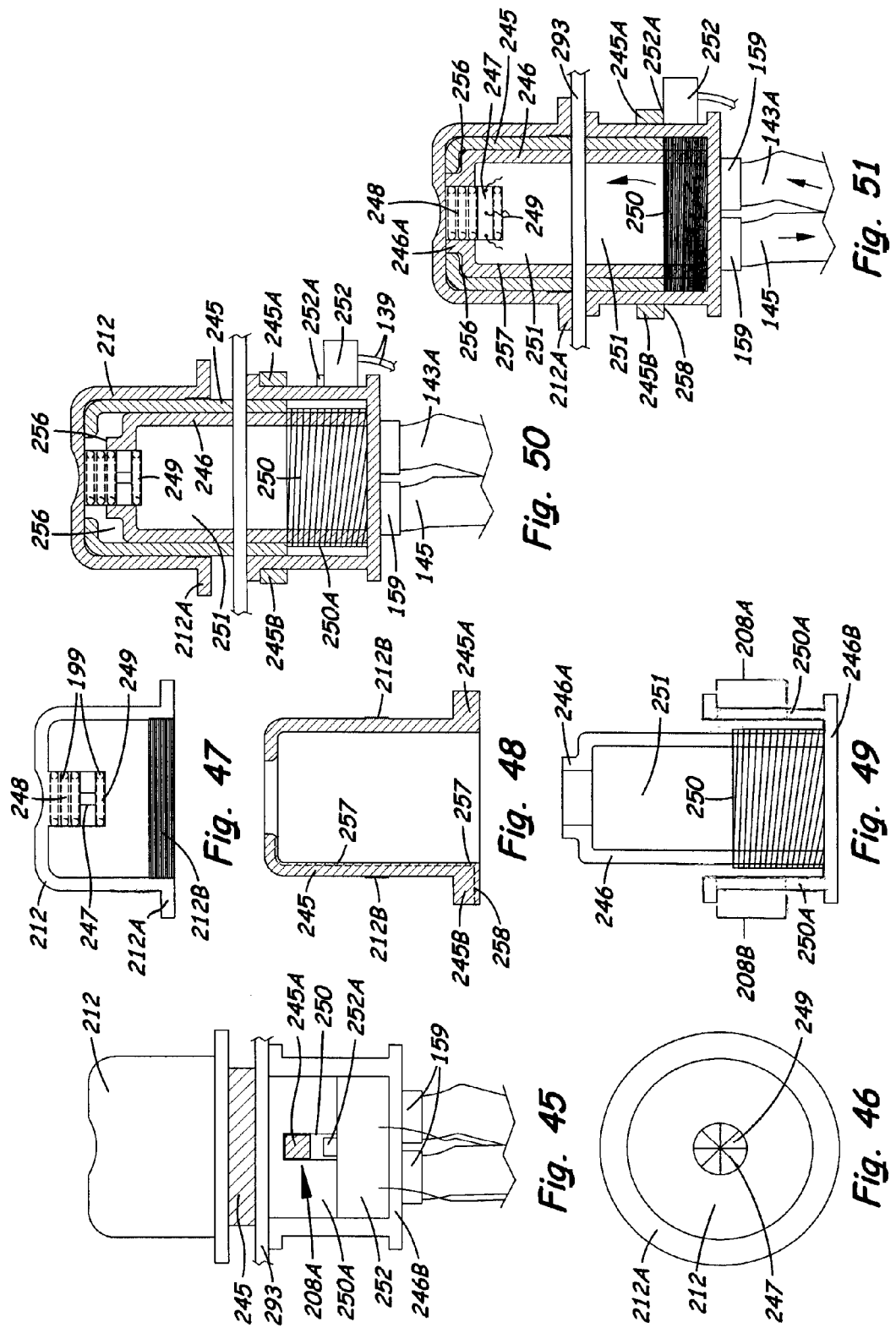

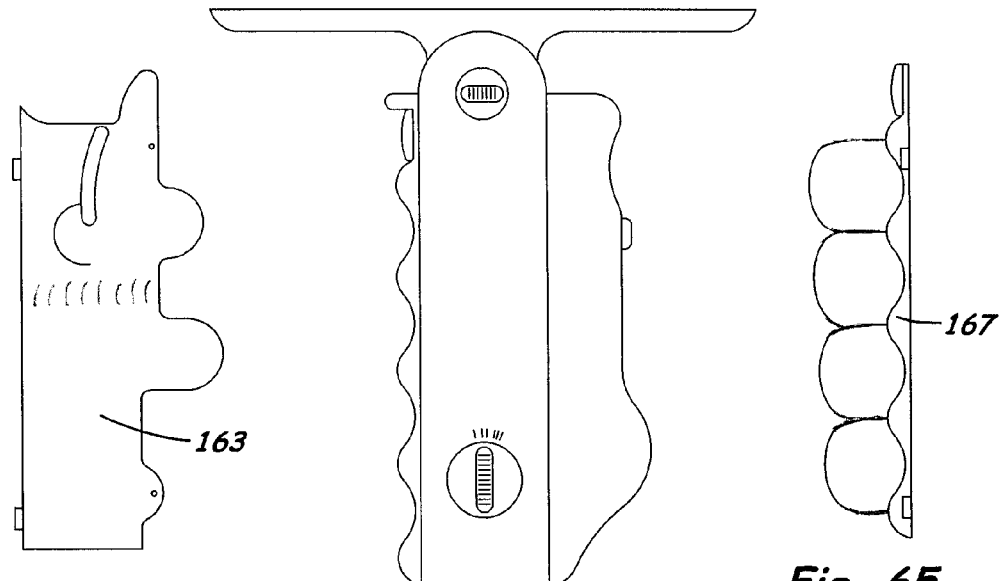
Fig. 63    Fig. 64    Fig. 65
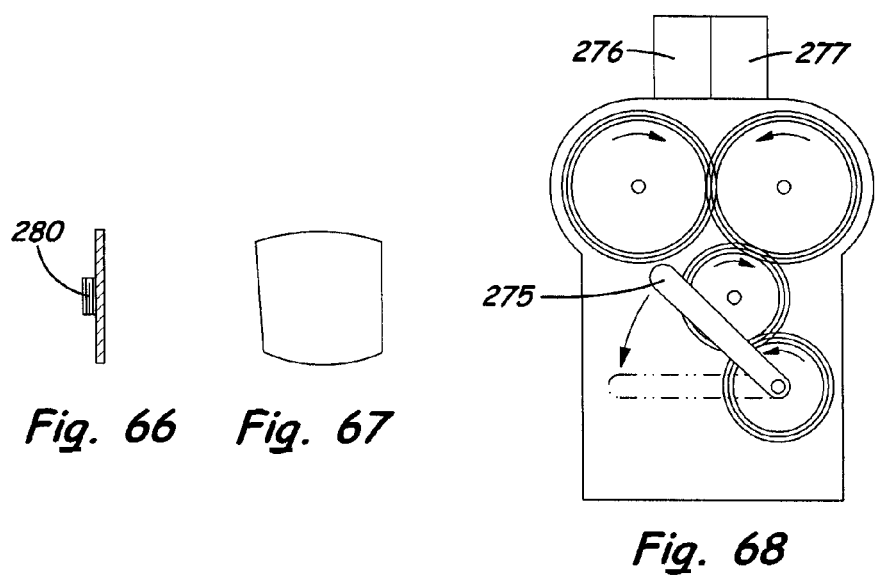
Fig. 66    Fig. 67
Fig. 68

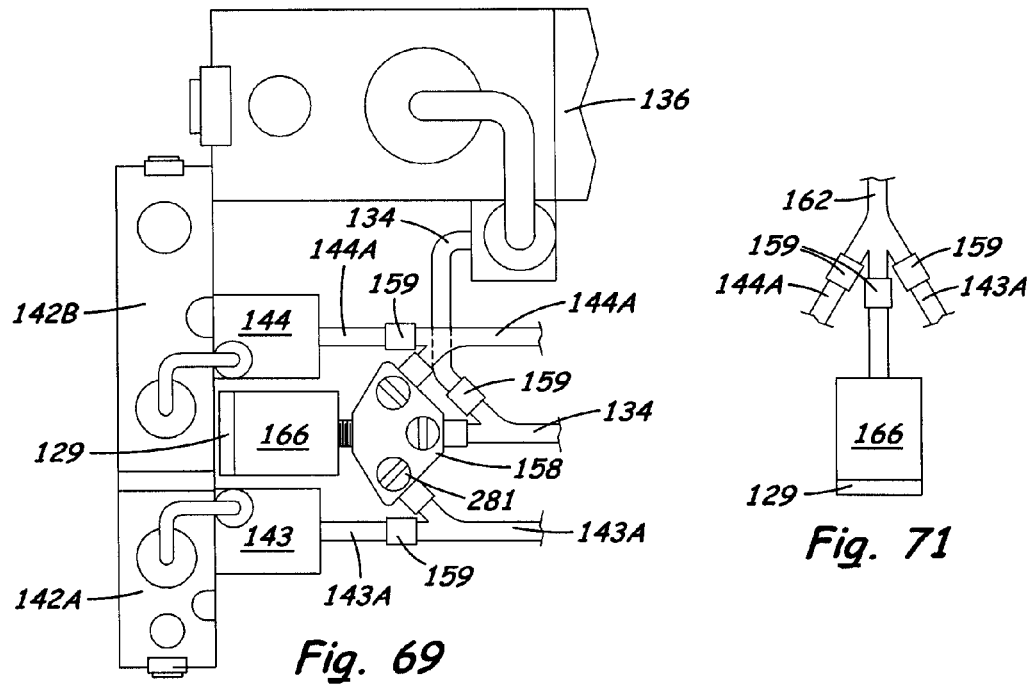
Fig. 69
Fig. 71
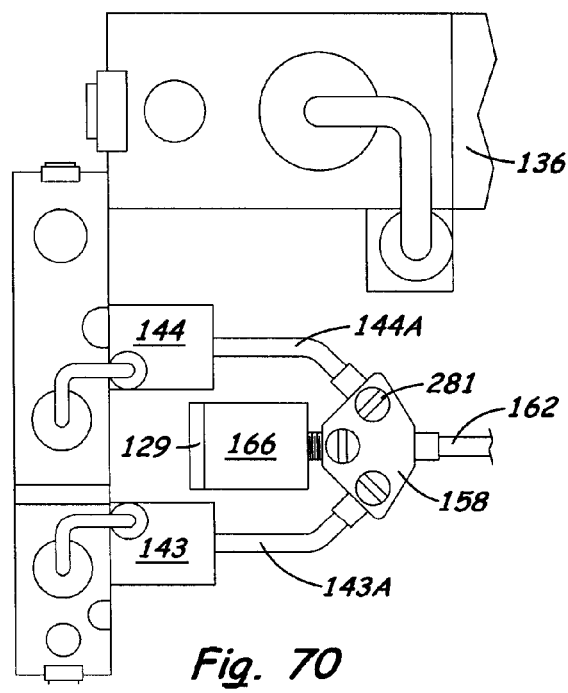
Fig. 70

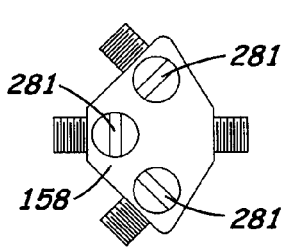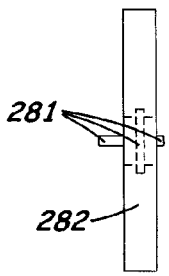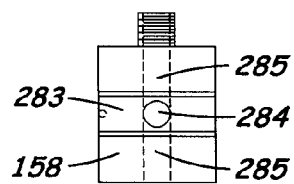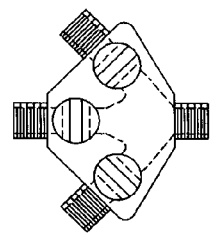
Fig. 72  Fig. 73  Fig. 74  Fig. 75
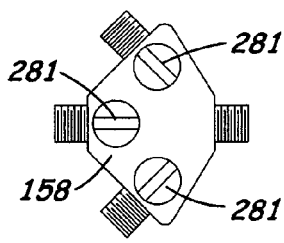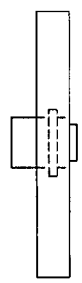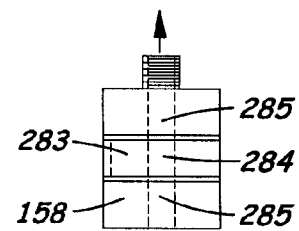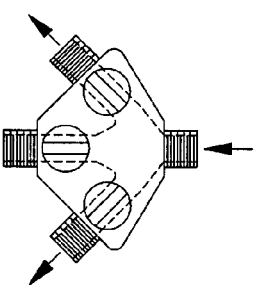
Fig. 76  Fig. 77  Fig. 78  Fig. 79
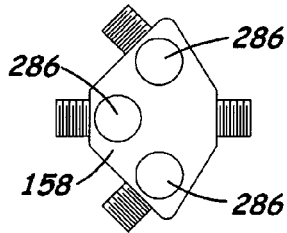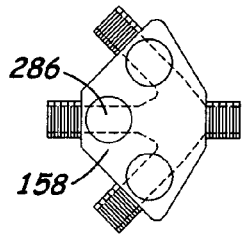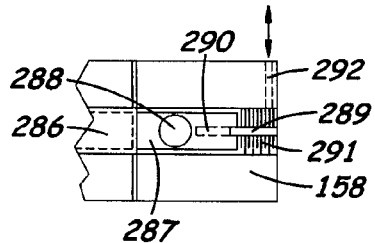
Fig. 80  Fig. 81  Fig. 82
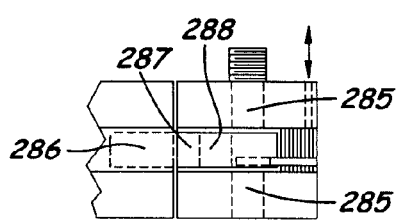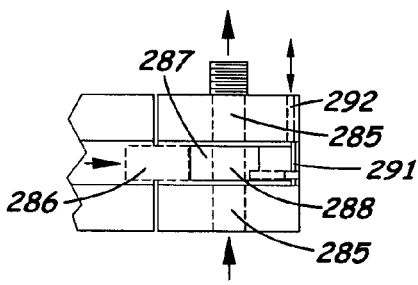
Fig. 83  Fig. 84

SELF-CLEANING SUCTION DEVICE

CROSS-REFERENCE TO RELATED APPLICATIONS

This application is a divisional of co-pending U.S. patent application Ser. No. 12/945,349, filed Nov. 12, 2010, which claims the benefits of U.S. Provisional Application No. 61/260,530 filed Nov. 12, 2009, the disclosures of which are hereby incorporated by reference in their entirety including all figures, tables and drawings.

STATEMENT REGARDING FEDERALLY SPONSORED RESEARCH OR DEVELOPMENT

Not applicable

REFERENCE TO SEQUENCED LISTING, A TABLE, OR A COMPUTER PROGRAM LISTING COMPACT DISC APPENDIX

Not applicable

BACKGROUND OF THE INVENTION

Suctioning devices are routinely used in the medical and dental fields, as well as in personal use settings, to remove unnecessary or waste fluids. Often such devices are used in conjunction with a surgical procedure where it is important to maintain a clean and sanitary environment. Removal of, for example, spittle or drainage from the site of a wisdom tooth extraction promotes healing and prevents the sockets from becoming infected. Periodically sanitizing/disinfecting and/or rinsing the affected area, enhances recovery from the surgical procedure. In a lab setting, neutralizing a spilled infectious and/or toxic compound, as it is being suctioned up, could greatly enhance safety. In a mobile, personal setting, it may be necessary to suction drool, due to an excessive drooling disorder.

Many suction devices have been described and focus on the importance of isolating the suctioned matter from the patient, user and/or the staff charged with disposing of it (see, for example; U.S. Published Patent Application Nos. 2004/0045980 A1; 2004/0072122 A1; 2005/0127103 A1; and 2006/0093990 A1; and U.S. Pat. Nos. 3,527,219; 4,966,580; 5,980,498; 5,104,315; 5,365,624; 5,984,145; 6,152,733; 6,314,960; 6,358,237; 6,409,048; 6,652,481; 6,851,275; 7,007,502; 7,059,852; and 7,118,377). These many devices are large and cumbersome and are designed to be used by physicians and dentists in an office setting. To maintain a clean environment at, for example, a surgical site, it is important that the suctioning end, be cleaned and sanitized before and after each use. Although self-cleaning devices have been described (see, for example, U.S. Published Patent Application No. 2005/0187528 A1), these devices do not necessarily focus on cleaning, sanitizing and/or disinfecting the suction tube end that contacts the surface to be suctioned before or after use. Further, they do not focus on sanitizing and/or neutralizing the suctioned matter directly after it enters the suction tube during use. The main focus of these devices is treating the suctioned matter after use and/or at the time it is collected.

A need remains for a simple, adaptable suction device, perhaps enhanced with a liquid-hydration and/or medicament delivery device, that functions with the user's safety in mind. Recent heightened concern of bacteria and airborne viruses, only adds to the sanitary necessity, of simply and automatically protecting yourself and/or patients, at the site of liquid delivery and suctioning.

All patents, patent applications, provisional patent applications and publications referred to or cited herein, are incorporated by reference in their entirety to the extent they are not inconsistent with the teachings of the specification.

BRIEF SUMMARY OF THE INVENTION

The invention is a suction device with a specialized, self-cleaning user's suction end. The interior of the user's suction end and suction tube are sanitized/neutralized during suction use. The interior and exterior of the user's suction end and interior of the suction tube are sanitized/neutralized before and after suction use.

A cover enclosing the user's suction end opens, to allow the user's suction end to emerge from a lower decontamination chamber, through sanitizing/neutralizing agents within a middle chamber, through an upper chamber, and to the user for suction use. After use, the user's suction end retracts through the upper chamber, encountering a narrowing, which scraps and collects material from the exterior of the user's suction end as it passes. During the course of the user's suction end rising and retracting through the middle chamber, its exterior is cleaned by means of cleaning seals, and sanitized by means of sanitizing/neutralizing agents isolated within the middle chamber. Once the cover seals closed, the upper and middle chambers are flushed with sanitizing/neutralizing agents, which are introduced into the upper and middle chamber by independent flow tubes. The sanitizing/neutralizing agents and collected debris are suctioned away. The user's suction end resides between uses, within the lower chamber, which enables the decontamination of the user's suction end by means of, for example, an UV-C germicidal light.

The suction device of the subject invention can include a liquid-hydration delivery device. The liquid-hydration delivery device, is incorporated into the device with a specialized mouthpiece which delivers one or more liquid-hydration and/or medicament choices to the user. Used, as well as new, sanitizing/neutralizing agents and/or liquid-hydration fluids, suction debris, and means to cause suction and sanitizing/neutralizing agents and/or liquid-hydration fluids to flow, are housed within a connected base unit.

BRIEF DESCRIPTION OF THE SEVERAL VIEWS OF THE DRAWING

FIG. 19 is a top elevational view of a preferred embodiment of a hand held suction device of the self-cleaning suction device of the subject invention.

FIG. 20 is a top elevational view of a preferred embodiment of a hand held suction device of the self-cleaning suction device of the subject invention.

FIG. 21 is a cross-sectional top elevational view of a preferred embodiment of a hand held suction device of the self-cleaning suction device of the subject invention.

FIG. 22 is an isolated view of a preferred embodiment of the covers of the hand held suction device of the self-cleaning suction device of the subject invention.

FIG. 23 is a front elevational view of the sliding suction tube containment unit of a preferred embodiment of a hand held suction device of the self-cleaning suction device of the subject invention.

FIG. 24 is a front elevational view of a right side cover piece of a preferred embodiment of a cover for a hand held suction device of the self-cleaning suction device of the subject invention.

FIG. 25 is a right side elevational view of the cover piece shown in FIG. 24.

FIG. 26 is a sectional right side view of FIG. 23 showing the cover piece of FIG. 24 removed.

FIG. 27 is a sectional right side view of FIG. 23.

FIG. 28 is a sectional view of FIG. 27 showing a preferred embodiment of a notched rotational housing of a preferred embodiment of a cover on a hand held suction device of the self-cleaning suction device of the subject invention.

FIG. 29 is a cross-sectional view of FIG. 28 showing a preferred embodiment of a notched rotational housing of a preferred embodiment of a cover on a hand held suction device of the self-cleaning suction device of the subject invention.

FIG. 34 is a perspective view of a preferred embodiment of a change-out base component of the suction/liquid hydration device of the subject invention.

FIG. 35 is a perspective view of a preferred embodiment of a change-out base component removed from the suction/liquid hydration base unit of the suction/liquid hydration device of the subject invention.

FIG. 36 is a side elevational view of a preferred embodiment of a change-out base component removed from the suction/liquid hydration base unit of the suction/liquid hydration device of the subject invention with the hand held suction/liquid-hydration attached.

FIG. 37 is a top plan view of a preferred embodiment of the liquid hydration device of the subject invention.

FIG. 38 is a front elevational sectional view of a preferred embodiment of a hand held liquid/hydration delivery device of the liquid hydration device of the subject invention.

FIG. 39 is a cross-sectional side elevational sectional view of the preferred embodiment of a hand held liquid/hydration delivery device shown in FIG. 38.

FIG. 40 is a side elevational sectional view of the preferred embodiment of a hand held liquid/hydration delivery device shown in FIG. 38 showing the covers open.

FIG. 41 is a cross-sectional side elevational sectional view of the preferred embodiment of a hand held liquid/hydration delivery device shown in FIG. 38 showing the covers open.

FIG. 42 is a sectional view of a preferred embodiment of the lock out pin flange of the hand held liquid/hydration delivery device shown in FIG. 38.

FIG. 43 is a left side elevational view of the preferred embodiment of a hand held liquid/hydration delivery device shown in FIG. 38.

FIG. 44 is a cross-sectional view of FIG. 43.

FIG. 45 is a cross-sectional right side elevational view of preferred embodiment of the liquid/hydration mouthpiece of the liquid hydration device of the subject invention.

FIG. 46 is a top view of a preferred embodiment of a mouthpiece cap of the liquid/hydration mouthpiece of the liquid hydration device of the subject invention.

FIG. 47 is a cross-sectional side view of the mouthpiece cap shown in FIG. 46.

FIG. 48 is a cross-sectional sectional view of a preferred embodiment of a mouthpiece slide unit of the liquid/hydration mouthpiece shown in FIG. 45.

FIG. 49 is a cross-sectional sectional view of a preferred embodiment of a tube capsule unit of the liquid/hydration mouthpiece shown in FIG. 45.

FIG. 50 is a cross-sectional left side view of the preferred embodiment of the liquid/hydration mouthpiece shown in FIG. 45 when not in use.

FIG. 51 is a cross-sectional left side view of the preferred embodiment of the liquid/hydration mouthpiece shown in FIG. 45 when in use.

FIG. 63 is a front elevational view of another preferred embodiment of a removable containment cover for the suction hand held device of the self-cleaning suction device of the subject invention having a thumb ring or strap.

FIG. 64 is a side elevational view of a preferred embodiment of a swivel grip for the suction hand held device of the self-cleaning suction device of the subject invention.

FIG. 65 is a side elevational view of a preferred embodiment of a finger grip for the suction hand held device of the self-cleaning suction device of the subject invention.

FIG. 66 is a sectional front elevational view of a preferred embodiment of a push bars on the hand held liquid/hydration delivery device of the liquid hydration device of the subject invention.

FIG. 67 is a sectional right side elevational view of a preferred embodiment of a push bar extension on the hand held liquid/hydration delivery device shown in FIG. 43.

FIG. 68 is a cross-sectional front sectional view of another preferred embodiment of a hand held liquid/hydration delivery device of the liquid hydration device of the subject invention.

FIG. 69 is a sectional side elevational view of a preferred embodiment of an air purging design for a base unit of the self-cleaning suction device of the subject invention.

FIG. 70 is a sectional side elevational view of a preferred embodiment of a multi-liquid delivery design for a base unit of the self-cleaning suction/liquid hydration device of the subject invention.

FIG. 71 is a sectional side elevational view of another preferred embodiment of a multi-liquid delivery design shown in FIG. 70.

FIG. 72 is a sectional side elevational view of a preferred embodiment of a rotating flow cylinder of a multi-flow chamber for a base unit of the self-cleaning suction/liquid hydration device of the subject invention.

FIG. 73 is a top elevational view of the upper portion of the rotating flow cylinder shown in FIG. 72.

FIG. 74 is a top elevational view of the lower portion of the rotating flow cylinder shown in FIG. 72.

FIG. 75 is a cross-sectional side elevational view of the rotating flow cylinder of a multi-flow chamber shown in FIG. 72.

FIG. 76 is a sectional side elevational view of a preferred embodiment of a multi-flow chamber for a base unit of the self-cleaning suction/liquid hydration device of the subject invention.

FIG. 77 is a top elevational view of the upper portion of the multi-flow chamber shown in FIG. 76.

FIG. 78 is a top elevational view of the lower portion of the multi-flow chamber shown in FIG. 76.

FIG. 79 is a cross-sectional side elevational view of the multi-flow chamber shown in FIG. 76.

FIG. 80 is a sectional side elevational view of a preferred embodiment of a multi-flow chamber with a push flow cylinder design for a base unit of the self-cleaning suction/liquid hydration device of the subject invention.

FIG. 81 is a cross-sectional side elevational view of the push flow cylinder multi-flow chamber shown in FIG. 80.

FIG. 82 is a bottom view of the push flow cylinder multi-flow chamber shown in FIG. 80 with a push cylinder in "non-flow" mode.

FIG. 83 is a front view of the push flow cylinder multi-flow chamber shown in FIG. 80 with a push cylinder in "non-flow" mode.

FIG. 84 is a front view of the push flow cylinder multi-flow chamber shown in FIG. 80 with a push cylinder in "flow" mode.

DETAILED DESCRIPTION OF THE INVENTION

The invention is a suction device with a unique user's suction end that is self-cleaning and self-sanitizing externally and internally before and after use, as well as self-sanitizing and/or neutralizing internally during use. The suction device can additionally be embodied with a liquid-hydration delivery device. The device of the subject invention comprises a base unit to provide suction/hydration for an attached hand held device which encloses the self-cleaning user's suction end.

The base unit of the device of the subject invention comprises at least one pump to create suction. Enabling suction within the enclosed chamber is accomplished either actively by a pump, and/or passively through air inlets in the containment unit of the hand held device and/or by means of air flow tubes from the base unit. The base unit further comprises a sanitizing/neutralizing reservoir and a waste reservoir. Means to empty the waste reservoir can include a simple drain plug to empty the reservoir by gravity, a pump or removable/disposable bags and/or containers. Means to refill the sanitizing/neutralizing reservoir can be accomplished by a refill spout and/or a removable/disposable insert. Additional pumps can be present in the base unit to provide power to deliver sanitizing/neutralizing agents to the containment unit. In a preferred embodiment, the base unit has a programmable control motherboard and corresponding components, allowing parameters such as suction time, suction pressure, sanitizing/neutralizing agent flow, volume and/or pressure, liquid-hydration delivery flow, volume and/or pressure to be controlled. All corresponding components may, for example be encompassed with check flow valves/flaps, flow/pressure sensors and/or liquid level sensors, a heating and/or cooling embodiments, an audio receiver and/or transmitter, GPS, remote control, and lights signaling functions/warnings/night use. The corresponding components can be powered by outlet, batteries and/or solar energy.

Figure 1:
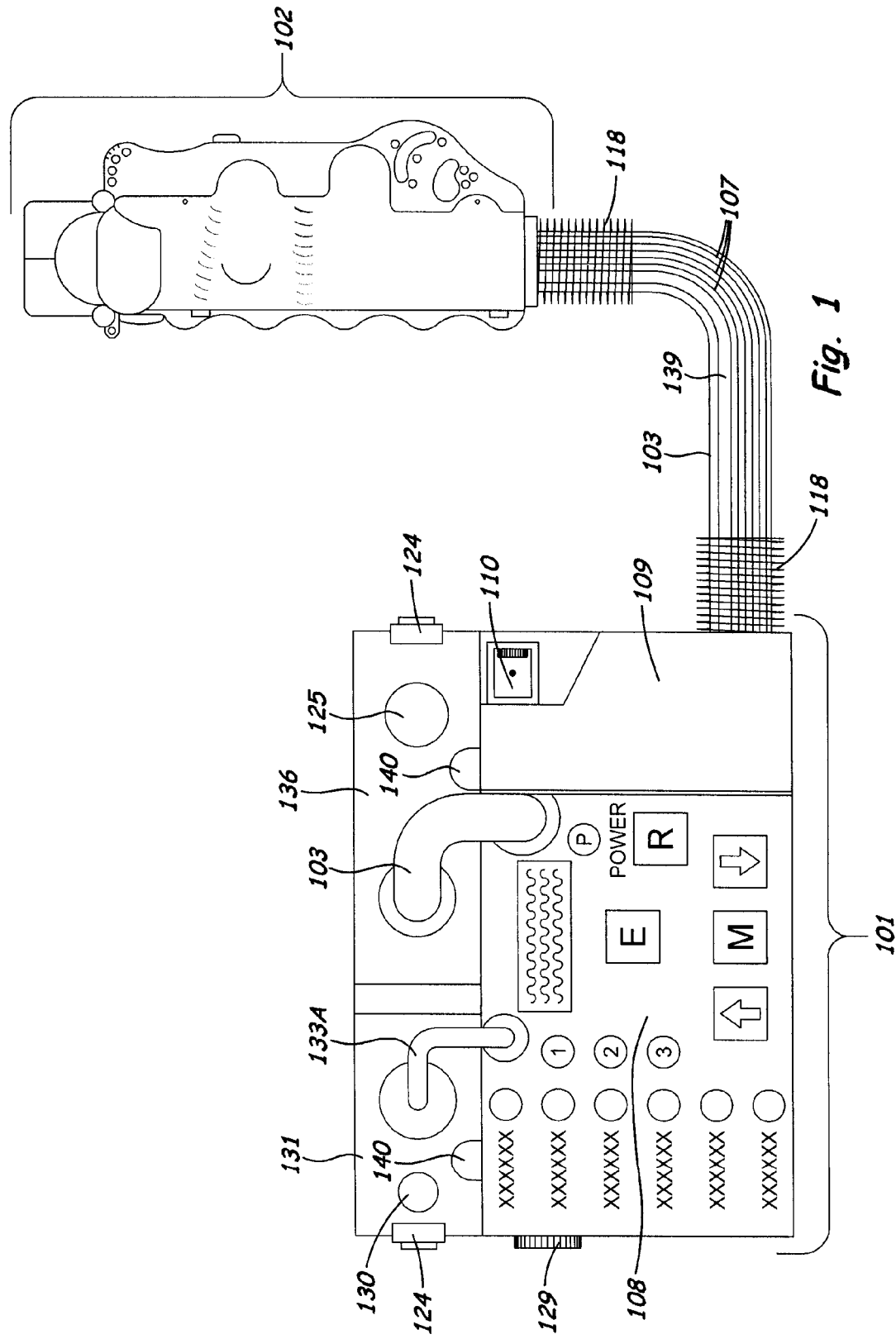
FIG. 1 is a top plan view of a preferred embodiment of the self-cleaning suction device of the subject invention.
Figure 33:
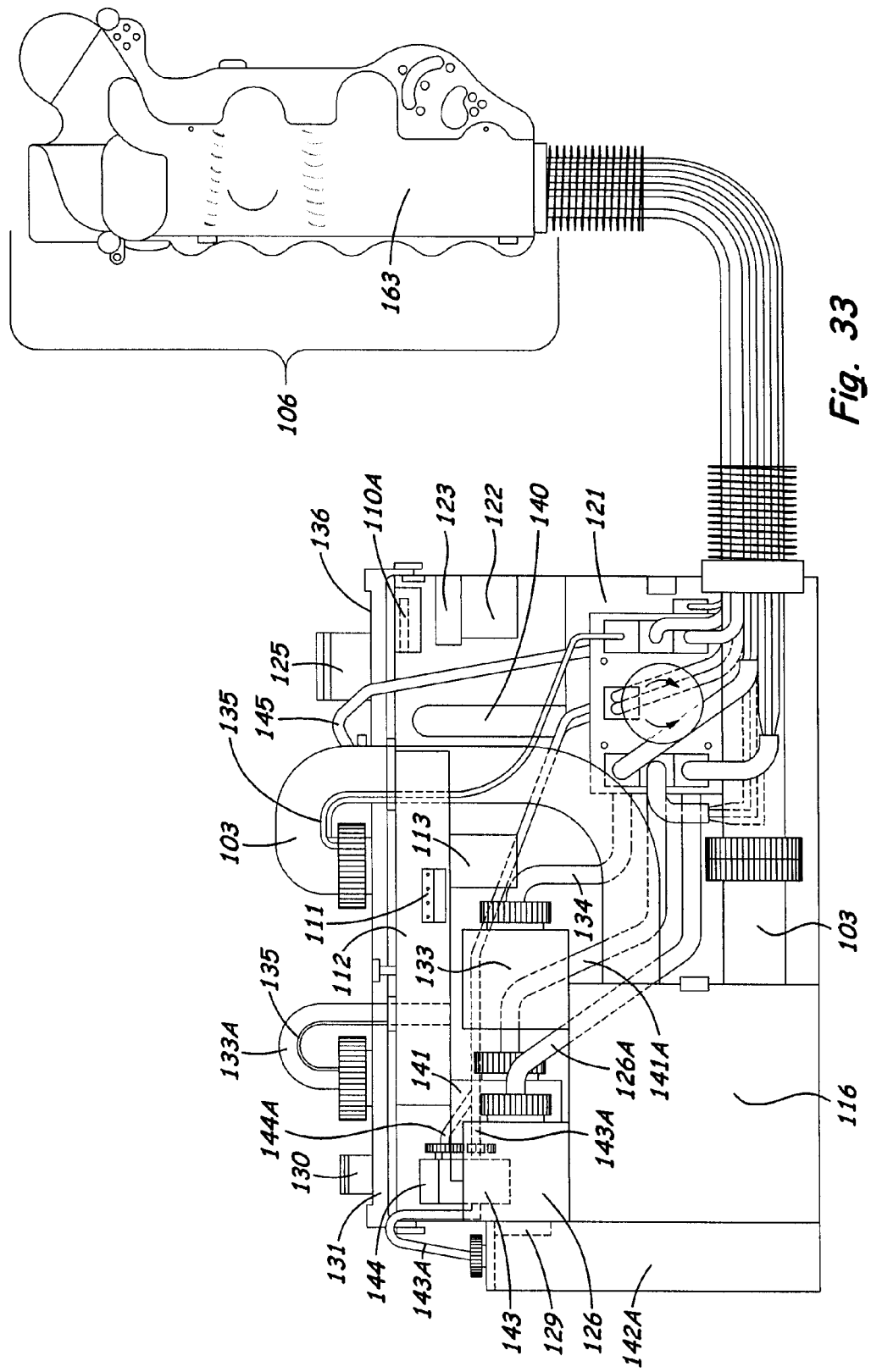
FIG. 33 is a side elevational view of a preferred embodiment of the self-cleaning suction/liquid hydration device of the subject invention showing a cross-section of the base unit.
Figure 52:
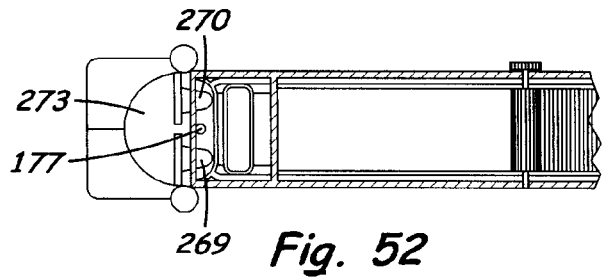
FIG. 52 is a front elevational view of another preferred embodiment of the hand held suction device of the self-cleaning suction device of the subject invention in partial cross-section and not in use.

Preferred embodiments of a suction base unit 101 shown in FIG. 1, a suction-liquid/hydration base unit 104 shown in FIG. 33, and a liquid/hydration base unit shown in FIG. 37 have corresponding components that are similarly numbered.

Specifically, preferred embodiments of the base units have a system control panel 108 (FIG. 1) adapted to a system control mother board 112 (FIG. 33), which has a universal serial bus (USB) port 111, a flash drive 113 and corresponding components, to enable manual and/or preprogrammed system function control. The subject device can be preprogrammed and/or controlled at the hand held device, the base unit and/or remotely, from a distant location to accommodate a specific user's needs.

Preferably, the base units have a password and/or manual (male) lockout 110 (FIG. 1), corresponding to a password and/or manual (female) lockout 110A (FIG. 33), to enable limited access within the base unit and/or removal of corresponding components. The base unit cover 109 (FIG. 1) opens and is removable along with a connected side cover (not shown) in FIG. 33.

In a preferred embodiment, systems are equipped with heat wires 160 (FIG. 36) and corresponding components to enable control of the temperature of the suction tube 103, flow tubes and hand held device.

A power source unit 121 (FIG. 33) provides solar and/or rechargeable/reusable battery power, and can provide power for a remote control 123 (FIG. 33) to establish communication between the base unit and the hand held device.

Base units can further comprise liquid level sensors, pressure sensors, suction tubes and corresponding pumps, air and liquid flow tubes and corresponding pumps, a purging tubes, audio ear plug in, air filters, ultra violet lights, check valves and/or flaps and holding containers.

Since it is intended for patient use, the base unit of the subject invention is preferably lightweight and portable, the base unit however can be larger and stationary if positioned for use in a hospital or dentist's office. It would be advantageous if the device was easily adapted for use by a number of users. Device parts can be modular and disposable to allow the device to be sent home with a recovering patient, used by the patient until treatment is no longer necessary, returned, reconfigured, and sent home with another patient. A separation of components design, works in harmony with an air flow purging system to enhance the removal of select components. A removable shell and/or glove on the body, not affecting function, can be easily disposed of when the patient returns the machine. Additionally, all parts of the body and perhaps the base unit and corresponding components, can be constructed of materials that can be sterilized by autoclaving and/or made of an antimicrobial material. Further, treating the interior of tubing and containers with a shedding compound would create a non-adhesive environment to facilitate internal cleaning.

The hand held devices of the self-cleaning suction devices of the subject invention are connected to the base units by a suction tube 103, power/signal source wires 139, multiple flow tubes 107 and preferably an anti-kink coiled wire 118. The anti-kink coiled wire 118 decreases or eliminates the kinking of connected components during use.

The hand held devices of the suction devices of the subject invention have a body, a cover, and a sliding suction tube containment unit comprising a suction tube, a user's suction end, flow tubes, an upper and middle sanitizing/neutralizing chamber, and a lower decontamination chamber. In a preferred embodiment, the cover is opened to activate emergence and presentation of the user's suction end at the head of the containment unit. Opening the cover can be accomplished by simple sliding the cover out of place, using a button mechanism, or it can be opened remotely, from, for example, the base unit. In a particularly preferred embodiment, the cover is bifurcated separated down a center line and pivots away from the center to reveal the emerging user's suction end. Applicant notes the cover is a convenient means to signal the user that the unit is being configured for use. The cover also keeps dust, dirt, and debris away from the enclosed user's suction end and the area from which it emerges. If however the user's suction end protrudes such that suction of the area can be accomplished with only the user's suction end, the cover may not be necessary since the user's suction end retracts completely within the hand held device.

The hand held device comprises one or more chambers. In a preferred embodiment, an upper chamber, nearer the head of the hand held device, collects debris from the exterior of the user's suction end, as the user's suction end retracts for storage. The user's suction end passes a narrowing between the upper and middle chambers which scraps/collects debris from the exterior of the retracting user's suction end. This scraping feature can be enhanced by altering the shape of the narrowing, or providing a resilient sweep around the narrowed section. During the course of the user's suction end rising/retracting through this narrowing and a narrowing between a middle and lower chamber, a sanitizing agents isolated within the middle chamber sanitizes the exterior of the rising/retracting suction end. In a preferred embodiment, the upper and middle chamber flush with a sanitizing/neutralizing agents upon the automatic closing of the cover. In the exemplified embodiment, this is accomplished with delivery flow tubes coordinating with pumps within the base unit. The flow tubes run within the body of the hand held device. The flushing sanitizing agents, the isolated sanitizing agents and the collected debris, within the upper and middle chambers, are suctioned away by the user's suction end. Suction within the enclosed environment of the upper and/or middle chambers is accomplished by means of passive and/or pumped air entering into the enclosed chambers. In an additional exemplified embodiment, sanitizing/neutralizing agents can be deposited into the interior of the user's suction end, and/or corresponding suction tube, during suction use as well as before and after suction use. This is accomplished by means of flow tubes which enter into flow channels within the walls of the suctioning user's suction end and/or suctioning tube. The user's suction end resides between uses, within the lower decontamination chamber, which is subjected to decontamination, and in the exemplified embodiment, an ultraviolet (UV) light.

Additional decontamination features can include the positioning of ultraviolet (UV) light shining into the chambers of the hand held device and the liquid containment containers in the base unit.

The hand held device holds the user's suction end, flow tubes, chambers and corresponding components within the body. Preferably, the body is configured to facilitate grip and user control. It can have an attachable tilting mechanism and/or be incorporated onto a robotic arm. Activation can be controlled from a base unit, or buttons can be placed on the body for easy access. The body can also be supplied with a variety of, rings, straps, bands, an attachable necklace and/or pull string to facilitate grip or secure the body to the user if the user is unable to control the body unassisted. The body can be configured with a variety of removable shapes and sizes of for example; grips, covers and body shells to enhance function ability as well as to accommodate for users who are physically challenged and/or impaired.

The suction hand held device 102 (FIG. 1), and the suction-liquid/hydration hand held device 106 (FIG. 30), can be equipped with an audio transmitter/receiver 219 (FIG. 3), system function indicators and indicator/warning lights 214, 222, 223 and 224 (FIG. 2), function control pressure switches 222A and 223A, and vibrating ability providing a reminder of function needs.

Figure 2:
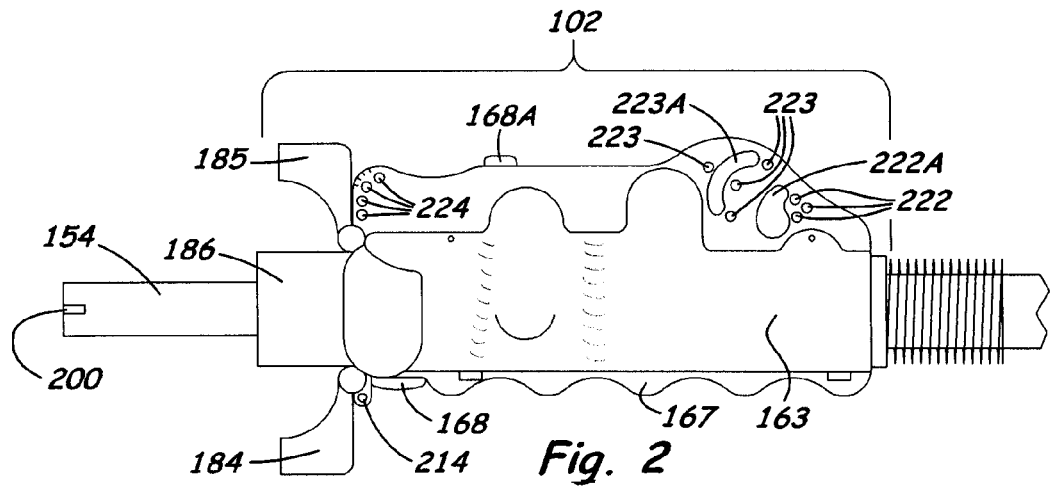
FIG. 2 is a front elevational view of a preferred embodiment of a suction hand held device of the self-cleaning suction device of the subject invention.

Preferred and necessary components of the hand held devices of the subject invention having suction functions are described below. Activation for suction use can be initiated by simultaneously pressing activation pressure switch 168 and safety pressure switch 168A (FIG. 2). A sliding suction tube 154 rises up to the user from a suction hand held device 102 (FIG. 2), or a suction-liquid/hydration hand held device 106 (FIG. 31) enabling suction use by the user. Upon deactivation, the sliding suction tube 154 automatically retracts, into an enclosed environment.

Figure 14:
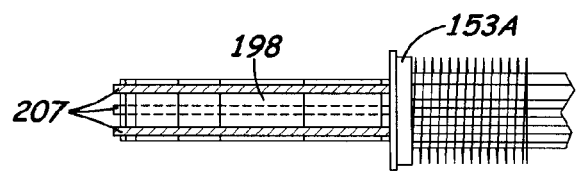
FIG. 14 is a front elevational view of the rigid suction tubes removed from a preferred embodiment of the suction hand held device of the subject invention.
Figure 15:
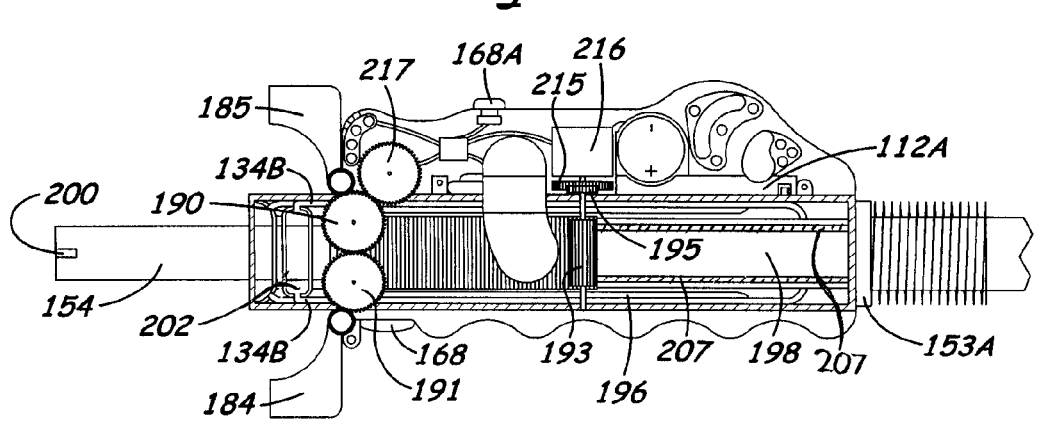
FIG. 15 is a cross-sectional front elevational view of a preferred embodiment of the suction hand held device of the subject invention.
Figure 16:
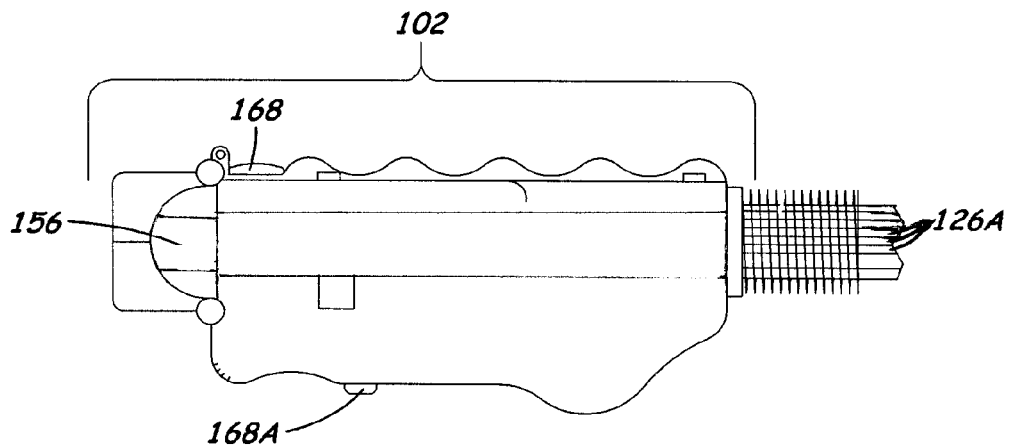
FIG. 16 is a rear elevational view of the preferred embodiment of the suction hand held device shown in FIG. 8.

FIGS. 9-15 show preferred embodiments of the sliding suction tube containment unit and its operation within the hand held device. The sliding suction tube 154 rises and retracts on stationary hollow open ended ridged suction tube 198 and stationary ridged flow tubes 207 (FIGS. 14 and 15). The tip end of the sliding suction tube 154 preferably has an anti-suction notch 200 (FIG. 15), to decrease and/or eliminate the sliding suction tube's 154 adherence to the surface being suctioned. A slot or hole in the side of the sliding suction tube 154, ridged suction tube 198 or suction tube 103, would likewise decrease adherence and can be used in combination with notch 200.

The sliding suction tube 154 upper tip end and anti-suction notch 200 resides within the cleaning seal 205 (FIG. 10), isolating the sliding suction tube 154 before and after use within the lower chamber 203 (FIG. 9) and isolating the lower chamber 203 from the middle chamber 202.

To equalize the pressure created by the upper portion of the sliding suction tube 154 rising from and retracting into the isolated lower chamber 203 (FIGS. 15 and 9), the lower chamber 203 comprises an air pressure equalizer channel 181 (FIG. 11) which travels from the interior of the lower chamber 203 and enters (not shown) into the passive air filtering chamber 174 (FIGS. 9 and 17), allowing filtered air to enter and to leave lower chamber 203 equalizing the air pressure within.

Figure 9:
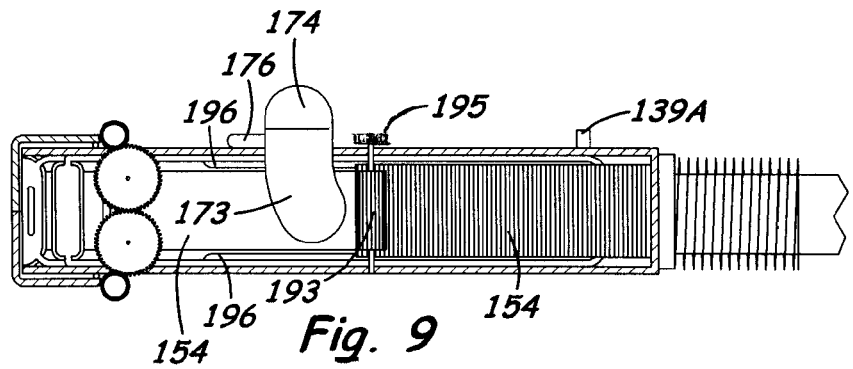
FIG. 9 is a cross-sectional front elevational view of a preferred embodiment of a sliding suction tube containment unit removed from the suction hand held device shown in FIG. 8.
Figure 11:
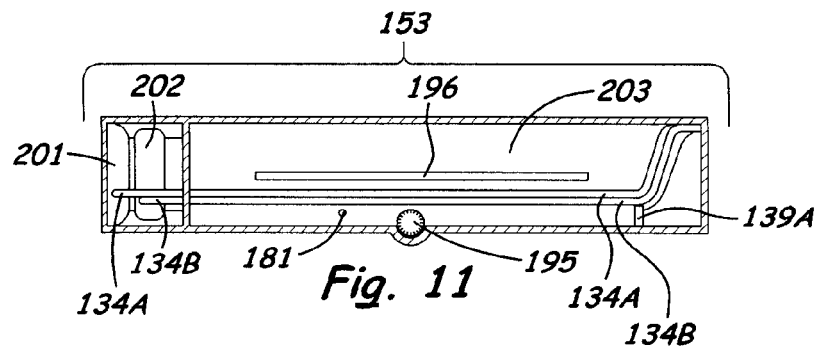
FIG. 11 is a cross-sectional right side elevational view of the sliding suction tube containment unit removed from a preferred embodiment of the suction hand held device of the subject invention.
Figure 12:
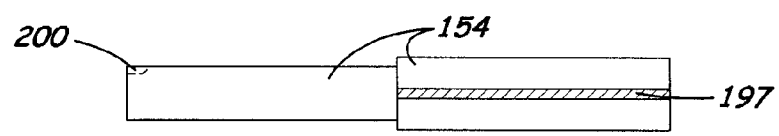
FIG. 12 is left side elevational view of the sliding suction tube removed from a preferred embodiment of the suction hand held device of the subject invention.
Figure 13:
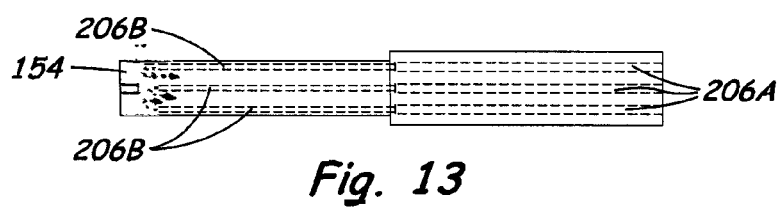
FIG. 13 is a cross-sectional front elevational view of the sliding suction tube shown in FIG. 12.

The guide channel 197 (FIG. 12) is an example of a notch or channel that can be placed in the side of the sliding suction tube 154. The guide channel 197 travels up and down on a channel guide 196 (FIG. 11). A corresponding guide channel located (not shown) on the opposite side of the sliding suction tube 154 likewise travels up and down on a corresponding channel guide (FIG. 9). In the exemplified embodiment, channel guides 196 are connected to the interior walls of lower chamber 203 (FIG. 11). The stability of the sliding suction tube 154 during movement is enhanced by the guide channels 197 traveling up and down on the channel guides 196. One skilled in the art would realize a number of methods of stabilizing the rising and retracting suction tube.

Figure 18:
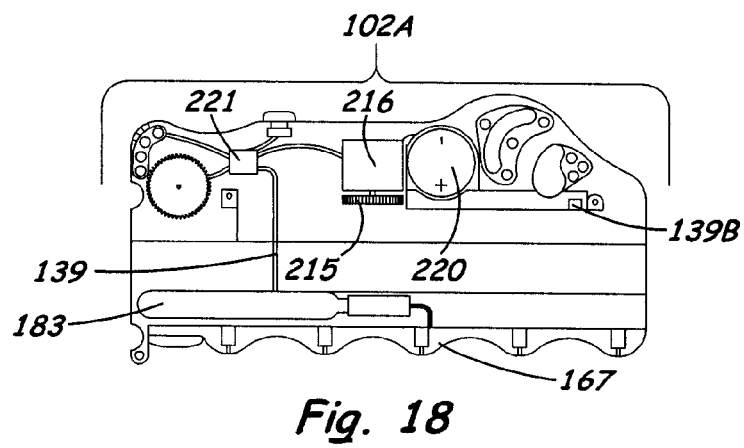
FIG. 18 is a cross-sectional front view of the hand held suction device component body removed from a preferred embodiment of the hand held suction device of the subject invention showing an isolated view of a germicidal light.

In the exemplified embodiment, the raising and lowering of the sliding suction tube 154 is accomplished by the teeth of the gear 193 rotating within the teeth and/or grooves in the lower portion of the sliding suction tube 154. The gear 193 located within the lower chamber 203 (FIGS. 9 and 15) is connected to gear 195 located on the outside of the lower chamber 203 (FIGS. 9 and 15) by means of a connected axel which travels through the side of the lower chamber 203. The axle rotates within the opposite interior wall. The teeth of the gear 195 set down into the teeth of the gear 215 to enable the removal and/or replacement of the containment unit 153 (FIGS. 9 and 15) from within the body (FIGS. 15 and 18).

Gear 195 is rotated by gear 215, which in turn is powered by motor 216. The motor 216 is powered by a power source in the hand held device, for example, battery 220 (FIG. 15) or a power source 121 located in the base unit (FIG. 33). One skilled in the art would realize there are a number of methods to manually and/or mechanically raise and/or lower the sliding suction tube 154 within the hand held device. The sliding suction tube 154 can, for example, rise and retract by multiple gears on the facing side and/or rear side of the sliding suction tube 154.

The shape and/or size of the sliding suction tube 154 and/or suction tube can be adapted to accommodate to the specific needs of the user, for example, corresponding components can conform to the size/shape of a catheter tube, enabling the suctioning of a tracheotomy.

When activation for suction use is initiated in the suction hand held device 102 (FIG. 1) and/or the suction-liquid/hydration hand held device 106 (FIG. 30) suction is created at the tip end of the sliding suction tube 154, by means of a suction pump 116 (FIG. 33). In the exemplified embodiment, the suction pump is a peristaltic pump which enables suction through one continual suction tube. The suctioned matter travels a course through the sliding suction tube 154 tip end, the suction tube 103 and into a contaminant collection container 136. The contaminant collection container has a filtered air outlet with a check valve or flap, an ultra violet light, and a removable cover with a cover latch 124. The contaminant collection container 136 can be emptied by removing a plug and disposing of the material properly, or the contaminant collection container can be lined with a replaceable bag which is removed and disposed of or be a replaceable component.

Figure 4:
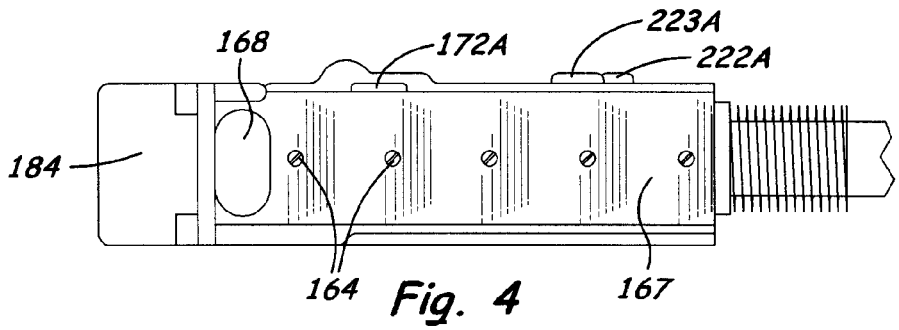
FIG. 4 is left side elevational view of the preferred embodiment of the suction hand held device shown in FIG. 2.
Figure 5:
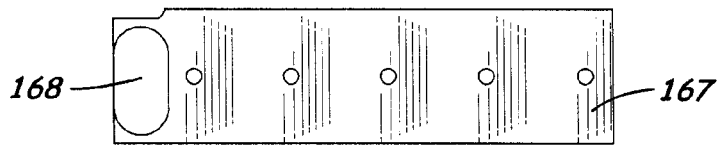
FIG. 5 is a left side elevational view of a removable finger grip applied to the preferred embodiment of the suction hand held device shown in FIG. 2.
Figure 6:
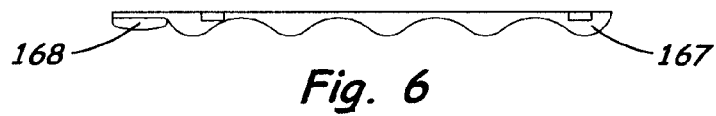
FIG. 6 is a front elevational view of a removable finger grip applied to the preferred embodiment of the suction hand held device shown in FIG. 2.

Suction within the enclosed environment of the chambers is accomplished by passive and/or pumped air entering into the chambers. In a preferred exemplified embodiment passive air is incorporated into the suction hand held device 102 (FIG. 1) and the suction-liquid/hydration hand held device 106 (FIG. 30) through a passive air cover inlet 172A (FIG. 4). Preferably, the hand held device has ridges or a rise above and below the passive air inlet 172A on the containment cover 163 to dissuade the thumb or fingers of the user from blocking air flow into the passive air inlet 172A.

Figure 7:
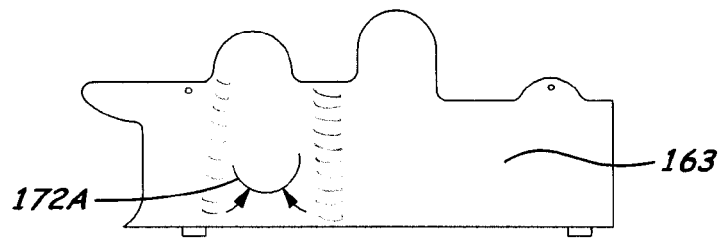
FIG. 7 is a front elevational view of a removable containment cover for a preferred embodiment of a suction hand held device of the self-cleaning suction device of the subject invention.
Figure 8:
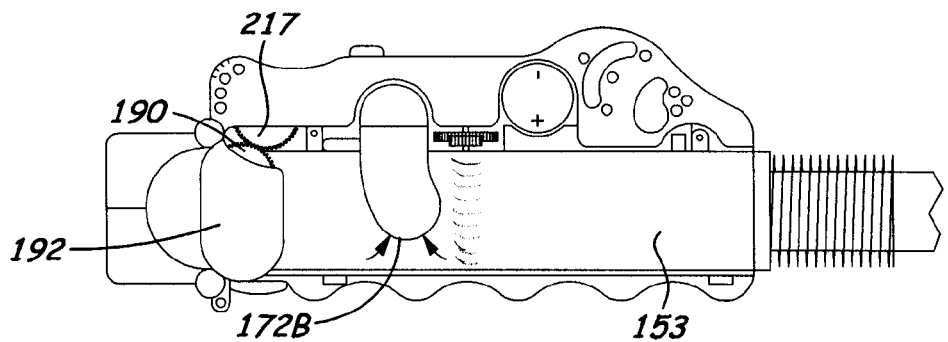
FIG. 8 is a front elevational view of a preferred embodiment of a suction hand held device with the containment cover removed.

When suction through the sliding suction tube 154 tip end is created within the enclosed upper chamber 201 and middle chamber 202 (FIG. 10), air flow (depicted by arrows in FIG. 7) is drawn in through the passive air cover inlet 172A, continues through the passive air chamber inlet 172B (depicted by arrows in FIG. 8), travels through the passive air chamber 173 (FIG. 9) and is filtered through the passive air filter within air filtering chamber 174. This air continues into the passive air flow connection channel 176, flows within the air flow channel 156 (FIG. 17) and up through the upper chamber air inlet 177 (FIG. 10), allowing air flow into enclosed upper chamber 201, through cleaning seal 204, into middle chamber 202, and the air travels into the suctioning sliding suction tube 154, and into contaminant collection container 136 in the base unit. FIG. 21 shows upper chamber air inlet 177 and flow tubes 134A entering upper chamber 201. The passive air filtering chamber 174 and upper chamber air inlet 177 have check valves or flaps allowing air flow in only one direction. Passive air flow in the exemplified embodiment can originate within, near and/or between the base unit and the upper chamber air inlet 177.

Pumped air can be introduced into the hand held device and is simultaneously activated at the initiation of suction within upper chamber 201 and middle chamber 202. In the exemplified embodiment, a pump 126 draws air in through filtered inlet 129, and into flow tube 126A (FIG. 33). The flow tube 126A can be split into, for example, three flow tubes 126A prior to exiting the base unit, and travel to the hand held device. The three flow tubes 126A are located between change-out base plate 148 and seal 146. FIG. 36 shows an exemplified embodiment of removable/replaceable components within the base unit and hand held device.

Figure 17:
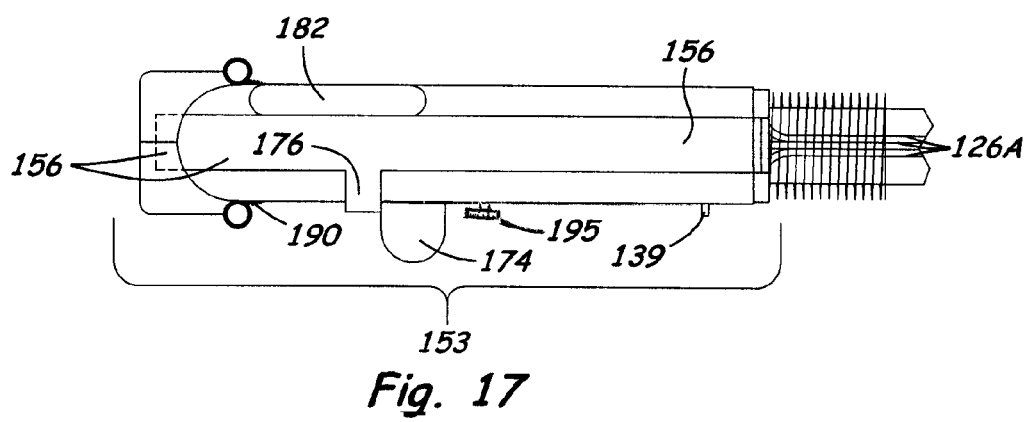
FIG. 17 is a rear elevational view of a preferred embodiment of a sliding suction tube containment unit shown in FIG. 9 also showing an isolated view of a germicidal light window.

FIG. 17 shows the three flow tubes 126A entering air flow channel 156 the air flow channel 156 connects into upper chamber air inlet 177. The passive air system has one directional flow check valves or flaps, allowing pumped air to travel past the passive air flow connection channel 176 (FIG. 17) up through the upper chamber air inlet 177, and into the upper chamber 201, enabling suction within an enclosed environment. The passive and pumped air systems can function together, and in turn enhance air flow through upper chamber air inlet 177 and into upper chamber 201, middle chamber 202 and the suctioning sliding suction tube 154 tip end.

The interior user's suction end of the device of the subject invention is sanitized during use. This is accomplished by introducing a sanitizing/neutralizing agent into the suction tube during use. Flow of suctioned debris is also enhanced by introduction of the sanitizing/neutralizing agent as the agents assist in moving suctioned debris through the suction tube.

Sanitizing/neutralizing agents travel from the sanitizing/neutralizing holding container 131 (FIGS. 1 and 33) through flow tube 133A. Pump 141 (FIG. 33) moves the agent through the flow tube 141A to the change-out base 147 and out the change-out base plate 148 (FIGS. 34 and 36). Flow tube 141A can be divided into three separate flow tubes 141A and travel to the hand held device. FIGS. 14 and 15 depict two facing ridged flow tubes 207 and a third ridged flow tube 207 (FIG. 14). The ridged flow tubes 207, travel up and along the side of the ridged suction tube 198. The flow channels 206A within the walls of the sliding suction tube 154 (FIG. 13) travel up and down on the ridged flow tubes 207 as the sliding suction tube 154 rises and retracts. The flow channels 206B continue on up from the flow channels 206A and open into the interior of the sliding suction tube 154, enabling delivery flow of sanitizing/neutralizing agents into the interior of the sliding suction tube 154, before and after suction use, as well as during suction use shown by the arrows in FIG. 13.

The exterior circumference of the ridged suction tube 198 and/or the interior circumference of the sliding suction tube 154, can have seals, for example, o-rings. Likewise, the exterior circumference of the ridged flow tubes 207 and/or the interior circumference of the flow channels 206A can have seals or o-rings.

The suction tube 103 and corresponding components, the ridged suction tube 198 and the ridged flow tubes 207 are connected to the containment unit base plate 153A and are removable/replaceable from the containment unit 153 (FIGS. 14 and 15). The sliding suction tube 154 is removable from within the containment unit 153. Openings through the containment unit base plate 153A correspond to the connection of the sliding suction tube 154, the ridged suction tube 198 and corresponding components. The flow tubes, power/signal source wires, and other components connected to the containment unit base plate 153A plug into their corresponding components located at or within the base of the containment unit 153. The removal of the containment cover 163 (FIG. 7) allows the removal/replacement of the containment unit 153 (FIG. 17) from within the suction hand held device 101 body (FIG. 18) along with and separately from removable/replaceable corresponding components. The removal of the containment cover 163 from the suction-liquid/hydration hand held device 106 (FIG. 33) likewise allows removal/replacement of components. One skilled in the art would realize a number of methods of disconnecting and reconnecting corresponding components enabling the removal/replacement of the desired components. The removal/replacement of components is facilitated by purging air through the system prior to removal/replacement of the desired components. One skilled in the art would recognize there are a number of methods to purge air through the subject system.

The sanitizing/neutralizing agents pumped into the suction tube can be of a varied chemical makeup. Multiple pumps can deliver the many agents through separate flow tubes which combine as they exit into the suctioning sliding suction tube 154. This design would enhance safety in a lab spill cleanup where suctioned toxic matter could be neutralized, by a mixture of neutralizing agents introduced into the interior of the suctioning suction tube tip end. Providing sanitizing/neutralizing agent to suction tubes can be adapted to current suction tubes and/or suctioning devices. Flow tubes can be added to deliver the agent into the interior of the current suction tubes.

Figure 30:
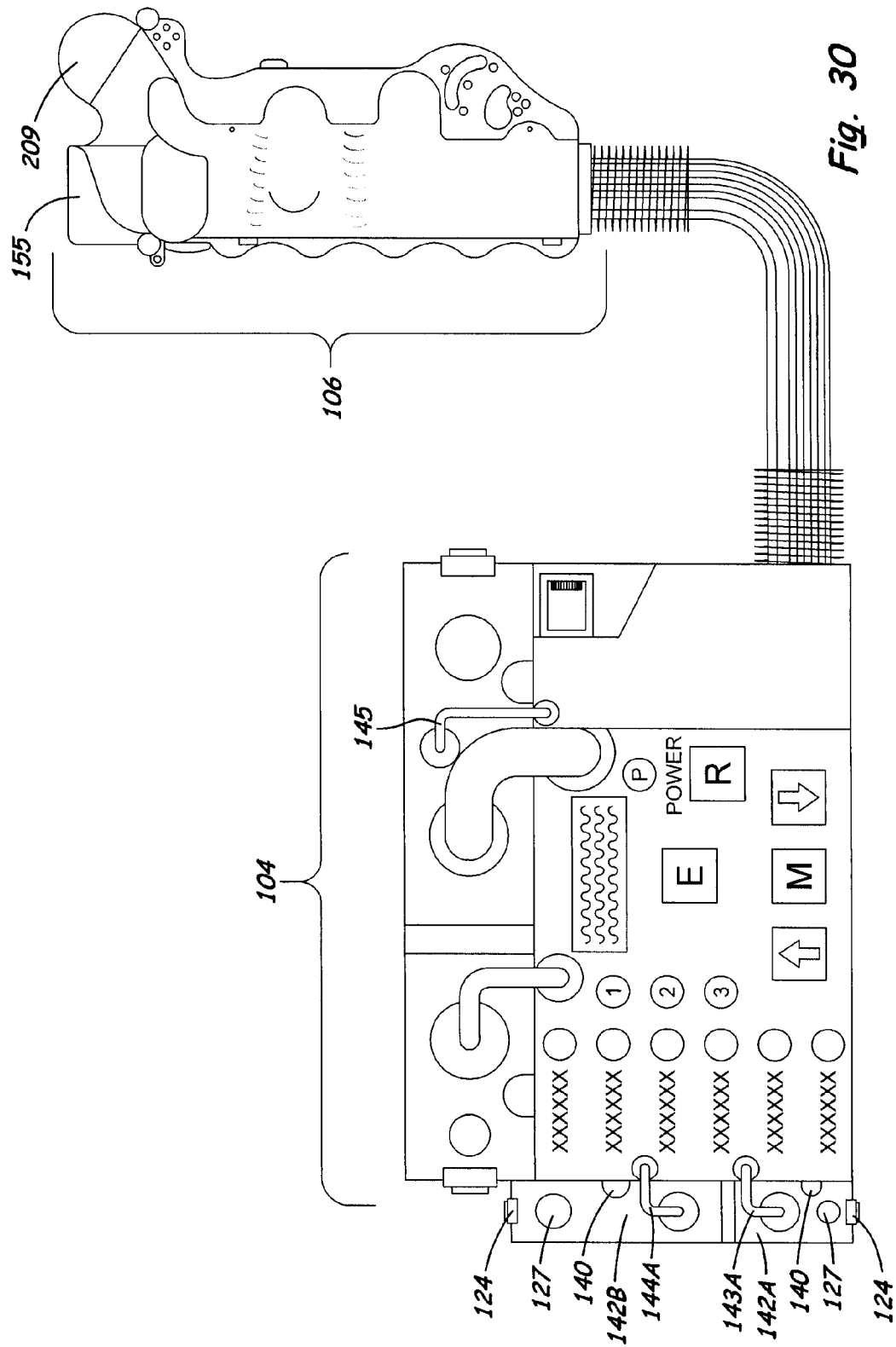
FIG. 30 is a top plan view of a preferred embodiment of the self-cleaning suction/liquid hydration device of the subject invention.

The self-cleaning suction device of the subject invention can further comprise a liquid/hydration delivery system (FIG. 30). Liquid/hydration delivery can be offered through a specialized mouthpiece, enabling liquid deliver to the user, in addition to a suction functioning embodiment.

FIG. 36 shows removable/replaceable components. The removable/replaceable components depicted in FIG. 36, correspond to the embodiment of replaceable/removable suction components shown in the suction device of FIG. 1.

Figure 10:
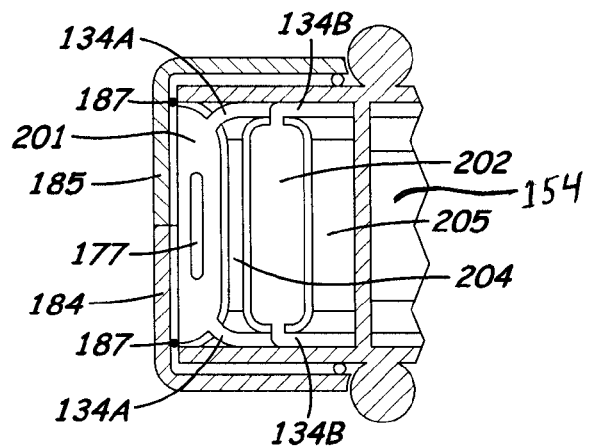
FIG. 10 is a cross-sectional sectional front elevational view of the distal end of the suction hand held device shown in FIG. 8.

FIG. 11 shows flow tube 134A and 134B entering into lower chamber 203. Flow tube 134A and 134B each divide into two separate flow tubes and travel up along the interior wall of the lower chamber 203 and into upper chamber 201 and middle chamber 202. FIG. 10 shows the two flow tubes 134B entering middle chamber 202 while FIG. 21 shows flow tubes 134A entering upper chamber 201.

Figure 31:
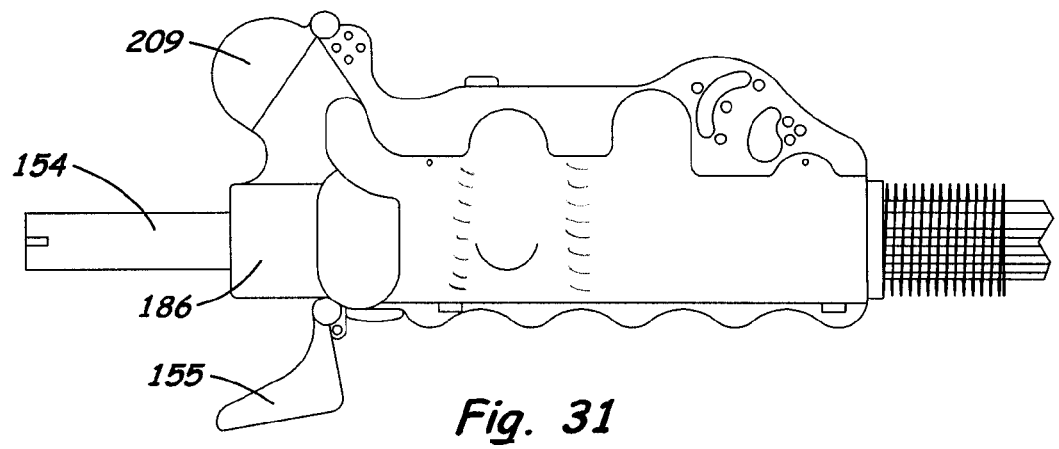
FIG. 31 is a front elevational view of a preferred embodiment of a hand held suction/liquid-hydration device of the self-cleaning suction/liquid hydration device of the subject invention with the sliding suction tube presented for use.
Figure 32:
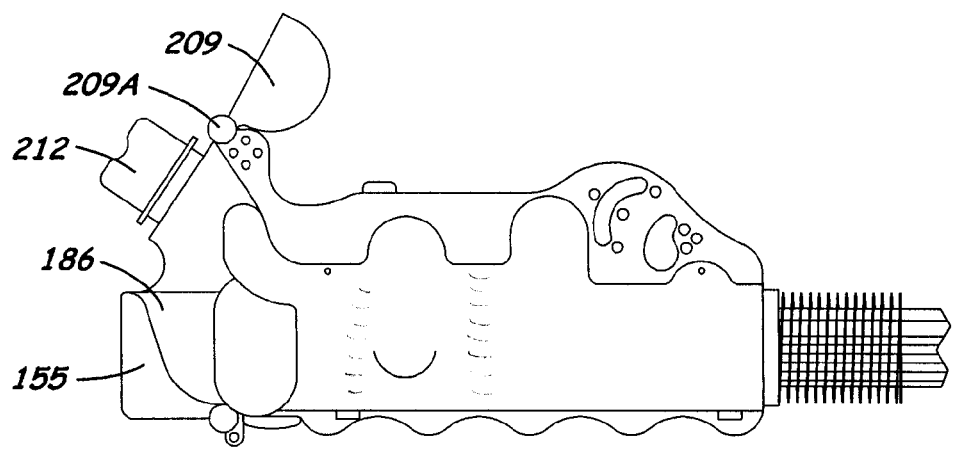
FIG. 32 is a front elevational view of a preferred embodiment of a hand held suction/liquid-hydration device of the self-cleaning suction/liquid hydration device of the subject invention with the liquid-hydration mouthpiece presented for use.

The upper outer edge of upper chamber 201 is connected to and surrounded by chamber housing unit 186 (FIG. 21). The chamber housing unit 186 comprises upper chamber 201, middle chamber 202. FIG. 31 shows the suction-liquid/hydration hand held device in suctioning mode. FIG. 32 shows the suction-liquid/hydration hand held device in a non-suctioning mode.

Before and after suction use in relation to the suction hand held device 102 and/or the suction-liquid/hydration hand held device 106, the sliding suction tube 154 tip end and corresponding anti-suction notch 200 reside within a cleaning seal 205 shown in FIG. 10. Looking down through the upper chamber 201 in FIG. 21 sliding suction tube 154 is surrounded and resides within the cleaning seal 205 which is located at the bottom of the middle chamber 202 shown in FIG. 10. This enables lower chamber 203 to be isolated from middle chamber 202. The hand held device component body 102A has a ultra-violet light 183 (FIG. 18).

The containment unit 153 has a solid clear ultra-violet light window 182 (FIG. 17). Ultra-violet light 183 shines through the ultra-violet light window 182 and into containment unit 153 decontaminating the sliding suction tube 154, lower chamber 203, middle chamber 202, upper chamber 201 and corresponding components within the containment unit 153. Preferably, the components within the containment unit are exposed to the ultra-violet light before and after suctioning by the user.

In a particularly preferred embodiment, the interior walls of the lower chamber 203 have a reflective quality, wherein the ultra-violet light entering the lower chamber 203 is reflected throughout the containment unit. The middle chamber 202, upper chamber 201, cleaning seal 205, cleaning seal 204 are composed of a material that allows ultra-violet light to shine through. The ultra-violet light is preferably a UV-C germicidal light.

Although the use of a germicidal light is preferred to sanitize components of the self-cleaning suction device of the subject invention, one skilled in the art would recognize there are a number of methods by which these components can be decontaminated.

Sanitizing/neutralizing agents enter the upper chamber 201 and middle chamber 202 through flow tubes 134A and flow tubes 134B flushing upper chamber 201 and middle chamber 202 and traveling through the sliding suction tube 154 tip end to the contaminant collection container 136 (FIGS. 10 and 33).

The suctioning sliding suction tube 154 rises from within the cleaning seal 205 and into the middle chamber 202. As the suctioning sliding suction tube 154 enter into the cleaning seal 204 (FIG. 10), the sanitizing/neutralizing agents entering into middle chamber 202 through flow tubes 134B and the sanitizing/neutralizing agents entering into upper chamber 201 through the flow tubes 134A ceases. The sanitizing/neutralizing agent remaining within middle chamber 202 is isolated from lower chamber 203 cleaning seal 205 and is isolated from upper chamber 201 by cleaning seal 204. The exterior of the suctioning sliding suction tube 154 is sanitized as the suctioning sliding suction tube 154 passes through the sanitizing/neutralizing agents isolated within middle chamber 202. The cleaning seal 204 scrapes the sanitizing/neutralizing agents from the exterior of the rising suctioning sliding suction tube 154. The sliding suction tube 154 suctions the remaining sanitizing/neutralizing agents from within upper chamber 201. The sliding suction tube 154 rises up through the upper chamber 201 and passes the synchronized opening left cover 184 and right cover 185 of the suction hand held device 102 (FIG. 2) or the opened cover 155 of the suction liquid/hydration hand held device 106 (FIG. 31), and is presented for suctioning use.

Upon deactivation by release of activation pressure switch 168 and safety pressure switch 168A suctioning sliding suction tube 154 retracts. The exterior of the suctioning sliding suction tube 154 is sanitized/neutralized as it retracts through the sanitizing/neutralizing agents isolated in middle chamber 203.

As the tip end of the retracting suctioning sliding suction tube 154 passes through the opening of chamber housing unit 186 (FIG. 21), and into upper chamber 201, left cover 184 and right cover 185 (or cover 155) seal around the opening and chamber housing unit 186 as suction continues.

Flow tubes 134A (FIG. 10) deliver a continual flow of sanitizing/neutralizing agent into sealed upper chamber 201, the sliding suction tube 154 suctions away the sanitizing/neutralizing agents and the foreign debris collected by cleaning seal 204. The cleaning seal 204 collects debris and foreign matter from the exterior of the suctioning sliding suction tube 154 as it retracts through upper chamber 201.

As the retracting suctioning sliding suction tube 154 tip end with anti-suction notch 200 travels through middle chamber 202, flow tubes 134B (FIG. 10) deliver a continual flow of sanitizing/neutralizing agent into middle chamber 202. The sanitizing/neutralizing agent is suctioned through the anti-suction notch 200 which enhances debris removal within the notch. Sanitizing/neutralizing agents are suctioned from middle chamber 202 and upper chamber 201. Sliding suction tube 154 tip end retracts into and resides within cleaning seal 205 and flow of sanitizing/neutralizing agents into upper chamber 201 and middle chamber 202 ceases. The sliding suction tube 154 tip end suctions away the sanitizing/neutralizing agents remaining within the upper chamber 201 and the middle chamber 202 and the corresponding debris collected by cleaning seal 205 and cleaning seal 204 to contaminant collection container 136 (FIGS. 1, 30 and 33) and suction ceases.

Applicant notes variable liquid flow direction into upper chamber 201 and/or middle chamber 202, in combination with, for example, a steam and/or spray would enhance the removal of debris. Further, multiple sanitizing/neutralizing holding containers in combination with multiple pumps would allow a variety of sanitizing, neutralizing, cleaning and/or flushing agents, to flow through separate independent flow tubes, and enter separately into upper chamber 201, middle chamber 202, and/or a multiple of sanitizing/neutralizing chambers.

The sanitizing/neutralizing holding container 131 shown in FIGS. 1 and 33 has a check valve/flap at filtered air inlet 130, an ultra-violet light 140, a liquid level sensor 135, and a removable cover latch 124 and flow tube 133A.

Contaminant collection container 136 (FIGS. 1 and 33), has a check valve/flap at filtered air outlet 125, an ultra-violet light 140, a liquid level sensor 135, a removable cover, bag insert within, and a removable suction tube 103. FIG. 33 is also shows a purging tube 145 to enable the liquid/hydration capabilities of the device shown in FIG. 33.

The function pressure switches 222 and 223A allow user control of a number of functions including, but not limited to, suction pressure, the rising/retracting of sliding suction tube 154, suction duration, disablement of the activation pressure switch 168 and safety pressure switch 168A, increasing/decreasing the sanitizing/neutralizing flow within the interior of sliding suction tube 154 during suction use and when applicable liquid/hydration capabilities.

Preferably, the hand held devices of the subject invention have covers that open automatically to enable the suction tube to rise and be presented for suction use by the user and close automatically when the suction tube retracts after suctioning use.

In a preferred embodiment, the covers open and close automatically by mechanical means. Gear cover 192 (FIG. 8) covers gear 190 and gear 191 (FIG. 15). Gear 190 and gear 191 rotate on axles connected to containment unit 153. In this embodiment, the cover has two pieces that separate at the centerline to reveal the user's suction end. This embodiment is best shown in FIGS. 19-29. Coordinating gears 190 and 191 (FIG. 8) reside behind gear cover 192 and allow the cover pieces to open synchronously. Each gear engages and turns a geared end 184B, 185B on the end of a rotational cylinder 184A, 185A on one end of each cover piece 184, 185. Each rotational cylinder sits within a notched housing 188, 189, respectively. Gears 190 and 191 engage geared ends 184B and 185B to open the cover. Gears 190 and 191 are turned by gear 217 (FIG. 15).

The teeth of gear 190, set down into and align with the teeth of gear 217. Gear 217 can rotate by a motor located directly below gear 217 powered by power source 220 or a power source within or near the base unit 101. In a preferred embodiment, teeth of gear 190 and gear 217 are angled. The angled teeth make removal/replacement these components easier.

A seal 187 lies on the underside of the left cover 185 and the right cover 184 (FIG. 20). The seal 187 encircling the outer edges of upper chamber 201 when the left cover 184 and the right cover 185 are closed (FIG. 10).

In another preferred embodiment, the suction liquid/hydration hand held device has one cover 155. The cover 155 (FIG. 31) has a connected (not shown) rotation cylinder with a geared end which rotates within a rotation housing enabling cover 155 to rotate open (FIG. 31) and close (FIG. 30) by movement of the gear 217 rotating gear 190 and gear 191. The cover 155 also has a circular seal (not shown) encircling upper chamber 201.

Figure 56:
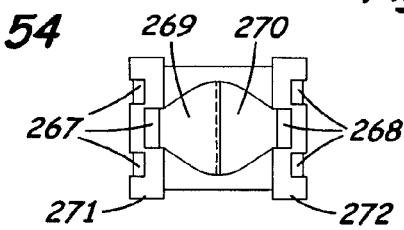
FIG. 56 is a left side elevational view of the left cover shown in FIG. 54.
Figure 57:
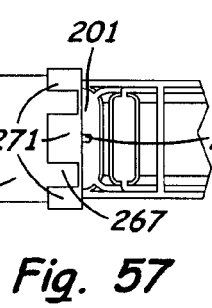
FIG. 57 is a sectional left side elevational view of the distal end of the hand held suction device shown in FIG. 52.
Figure 58:
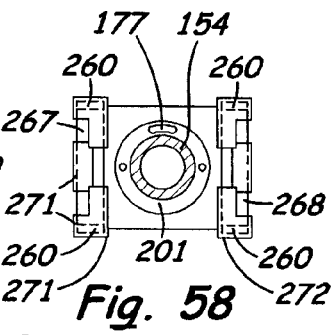
FIG. 58 is a cross-sectional top view of the hand held suction device shown in FIG. 52.
Figure 59:
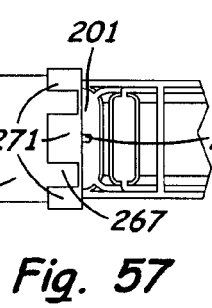
FIG. 59 is a partial cross-sectional top view of the hand held suction device shown in FIG. 52.
Figure 60:
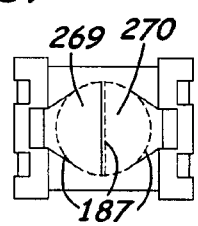
FIG. 60 is a cross-sectional top view of the hand held suction device shown in FIG. 59.
Figure 61:
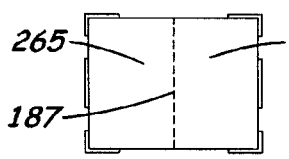
FIG. 61 is top elevational view of the hand held suction device shown in FIG. 52.
Figure 62:
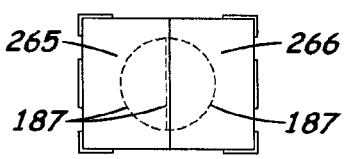
FIG. 62 is a partial cross-sectional top view of the hand held suction device shown in FIG. 52.

FIGS. 52 through 62 show another preferred embodiment of a suction cover. In this embodiment, the sliding suction tube 154 pushes the cover open as it rises for use. Left cover 265 and right cover 266 part to expose the user's suction end. A left rotation cylinder 267 on the left cover 265 rotates within a left rotation cylinder enclosure 271. The center section of the rotation cylinder enclosure 271 (FIG. 57) encircles the center section of the rotation cylinder 267 and engages a slot above the center of the rotation cylinder 267 (FIG. 56). The rising tube encounters push flaps 269 and 270 that move the cover. The corresponding opposite ends of the left rotation cylinder 267 and the right rotation cylinder 268 reside and rotate within the opposite end sections of the corresponding left rotation cylinder enclosure 171 and corresponding right rotation cylinder enclosure 172, enabling both cover pieces to rotate in unison and expose the rising user's suction tip end.

Figure 53:
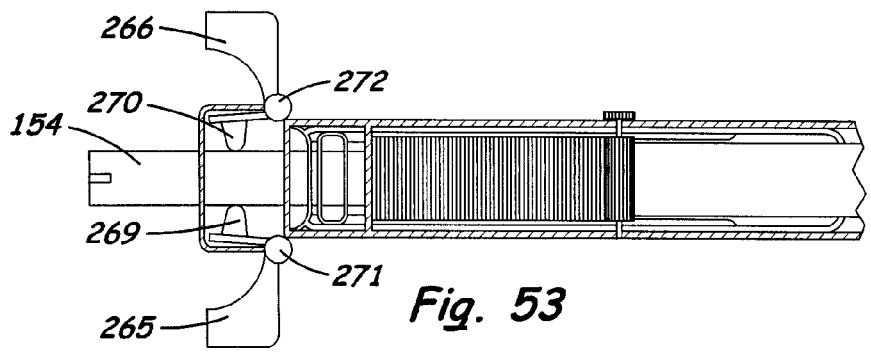
FIG. 53 is a front elevational view of FIG. 52 in use.
Figure 55:
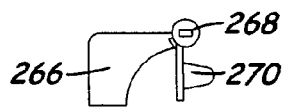
FIG. 55 is a sectional side view of the right cover of the hand held suction device shown in FIG. 52.
Figure 54:
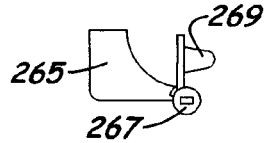
FIG. 54 is a sectional side view of the left cover of the hand held suction device shown in FIG. 52.

Push flap 269 and push flap 270 remain within the push flaps housing 273 before suctioning use (FIG. 52) as well as during suctioning as depicted within FIG. 53. Half circular seals 187 connected to the underside of each corresponding left cover 265 and right cover 266 seal around the circular opening located within the top of the push flaps housing 273 (FIG. 58), when the left cover 265 and right cover 266 are closed. The sliding suction tube 154 rises and retracts through the circular opening within the top of the push flaps housing 273.

Operably connected tension springs 260 end portions of left rotation cylinder 267 and right rotation cylinder 268 open under tension and close under tension as the sliding suction tube 154 rises and retracts.

In addition to providing suction, the device of the subject invention can include a liquid-hydration delivery device. At least one delivery tube to the liquid-hydration delivery device mouthpiece delivers hydrating fluids such as water, or sports drinks. Alternatively, the delivery tube can deliver medicaments. Further, should the area being suctioned need to be flushed, a flushing solution, such as saline, hydrogen peroxide, or mouthwash, could be delivered by at least one delivery tube. Delivery of fluids to the mouthpiece can be orally drawn up and/or powered by, for example, a pressurized system or pumps. In a preferred embodiment the liquid-hydration delivery device is incorporated with a specialized mouthpiece. In an exemplified embodiment, multiple delivery tubes can be provided to deliver a number of fluid choices or alternatively, a purging system allows a tube(s) to be purged of the delivery fluid and replaced by a new fluid. The mouthpiece can be fitted with covers, which can be pushed to the side, removed or manually and/or mechanically opened. The liquid-hydration delivery mouthpiece can be included in its own hand held device, or the mouthpiece can be included in the hand held device of the suction device.

A liquid/hydration specialized mouthpiece, when pressed down allows a user to receive a liquid, a hydrating fluid, a medicament and/or a nutritious substance. A preferred embodiment of the specialized liquid/hydration mouthpiece is shown in FIGS. 50 and 51. FIG. 50 shows the specialized liquid/hydration mouthpiece in a "non-use" (no-flow) mode. FIG. 51 shows the specialized liquid/hydration mouthpiece in an "in-use" (flow) mode.

The component pieces shown in FIGS. 47, 48, and 49 interlock to form the specialized liquid/hydration mouthpiece. FIG. 49 shows tube capsule unit 246 and spring enclosure 250A connected to the tube capsule unit base 246B. Tube capsule unit 246 is a circular hollow cylinder. FIG. 48 shows mouthpiece slide unit 245. The mouthpiece slide unit 245 is a hollow open ended cylinder, formed in shape and size to slide onto tube capsule base unit (FIG. 49). FIG. 49 also shows air channel guide slot 208B and the power connect guide slot 208A located in spring enclosure 250A. The power connect flange 245A is connected to the mouthpiece slide unit 245 as shown in FIGS. 45 and 48. The power connect guide slot 208A, is an opening through spring enclosure 250A (FIG. 45). The power connect flange 245A travels through the spring enclosure in power connect guide slot 208A and rests on spring 250. It is pressed up under spring tension against the top of power connect guide slot 208A. An opposing view of FIG. 45 (not shown) would show air chamber flange 245B traveling through the air channel guide slot 208B and resting under spring tension on spring 250 and pressed up against the top of the air channel guide slot 208B.

Continual spring tension on the bottom side of the mouthpiece slide unit 245 causes the mouthpiece slide unit 245 to remain pressed up impeding flow and closing the mouthpiece to flow. The spring tension also causes the mouthpiece slide unit 245 to return to the no flow position when pressure on the mouthpiece cap 212 is released.

FIG. 47 shows mouthpiece cap 212. The mouthpiece cap 212 has a honeycomb 247, honeycomb housing 248, honeycomb base plate 249, seals 199, mouthpiece cap flange 212A and threads 212B. FIG. 46 is a top side facing view of the mouthpiece cap 212 and shows the cylindrical component.

The honeycomb housing 248 is a hollow cylinder shaped component with seals 199 circling the outer circumference of the honeycomb housing 248. The pie-shaped honeycomb 247 is connected to the solid honeycomb base plate 249. The openings of the pie-shaped honeycomb 247 travel through the center of the mouthpiece cap 212 (FIG. 46) and open up from between the honeycomb housing 248 and the honeycomb base plate 249. The mouthpiece cap 212 is removable/replaceable so that it can be cleaned and/or replacement with a variety of shapes and sizes of mouthpiece caps 212 focusing on the specific needs of the user.

In the exemplified embodiment mouthpiece cap 212 screws onto mouthpiece slide unit 245 by threads 212B. When the mouthpiece cap 212 is screwed onto mouthpiece slide unit 245, the bottom portion of the honeycomb housing 248 and seal 199, the honeycomb 247, and the honeycomb base plate 249 and seal 199 rotate down into and are surrounded by the hollow cylindrical shape of stop flow housing 246A. This isolates honeycomb 247 openings from the interior of the liquid delivery chamber 251 preventing flow.

An air chamber 256 surrounds the tube capsule 246 and exists below the mouthpiece slide unit 245 creating an isolated air chamber 256 within the mouthpiece. Mouthpiece cap 212 presses down and creates a greatly diminished air chamber 256 (FIG. 51). Air chamber channels 257 with air filters 258 in mouthpiece slide unit 245 allow air to flow from and into air chamber 256.

Liquid delivery to the specialized mouthpiece is accomplished by one or more flow tubes embodied with check valves or flaps traveling from a connected container. The specialized mouthpiece can be configured so that liquid/hydration can be drawn up orally, or be delivered under pressure by pump from a connected container.

To use mouthpiece cap 212 the cap is pressed down, and power connect flange 245A depresses pressure switch 252A activating the power signal unit 252 and signaling the base unit to initiate liquid flow to the mouthpiece (FIG. 51). Flow tube 143A with a check valve and/or flap connects through the tube capsule unit base 246B allowing liquid flow into liquid delivery chamber 251. Multiple flow tubes allow liquid flow into liquid delivery chamber 251 (FIG. 36).

Figure 3:
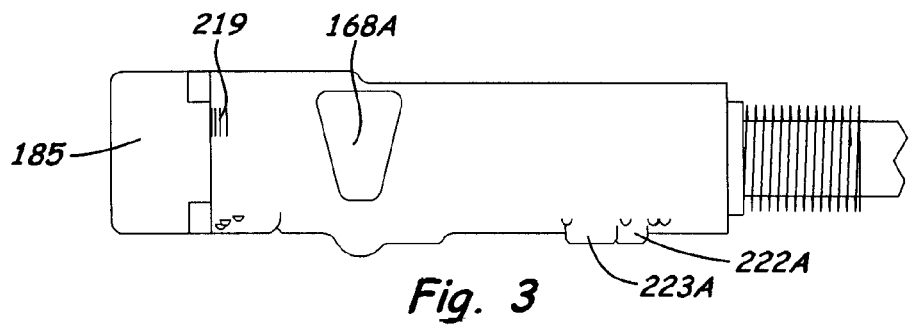
FIG. 3 is right side elevational view of the preferred embodiment of the suction hand held device shown in FIG. 2.

In the exemplified embodiments, flow tube 143A draws liquid from a liquid holding container 142A with air filter 127 having check valves or flaps, a UV-C germicidal light 140, a cover release 124, a connected flow tube 143A and the replaceable bag and/or container within. Pump 143 (FIG. 33) when signaled by the mouthpiece cap 212 being pressed down, pumps liquid through flow tube 143A to the liquid/ hydration specialized mouthpiece allowing liquid flow through the check valve and/or flap 159, into the liquid delivery chamber 251, through the honeycomb 247 and to the user (FIG. 51). When mouthpiece cap 212 is pressed down signal unit 252 signal the system control motherboard 112 by power/ signal source wires 139 connected to the base unit. The signal unit 252 is powered by the battery 220 (FIG. 18) and signals the system control motherboard 112 (FIG. 33) by remote control 123 (FIG. 3).

The liquid/hydration specialized mouthpiece is preferably fitted with a purge tube 145 with check valves and/or flaps. The purge tube 145 travels from the liquid delivery chamber 251 and empties into a contaminant collection container 136 (FIGS. 33 and 37). When not in use liquid flowing through the flow tube 143A (FIG. 44) enters into the liquid delivery chamber and travels through the one-way check valve/flap of the purge tube 145 to contaminant collection container 136. Flow through the flow tube 144A (FIG. 44) flushes out the previous liquid from within liquid delivery chamber 251, allowing another liquid choice for the user. In the event of excessive flow pressure within the liquid delivery chamber 251 during liquid/hydration use pressure sensitive check valve/flap of purge tube 145 would release the excess liquid into purge tube 145. Check valves and/or flaps are pressure sensitive.

Removing/replacing the mouthpiece cap 212 from the liquid/hydration specialized mouthpiece is facilitated by first purging air through the liquid flow tubes, through the liquid delivery chamber 251, through the check valve/flap of purge tube 145, and components continuing to the contaminant collection container.

Full depression of the mouthpiece cap 212 pushes the mouthpiece cap flange 212A down to mouthpiece mounting platform 293 (FIG. 51). FIG. 44 shows the liquid/hydration specialized mouthpiece connected to a mounting platform 293 the mouthpiece is integral with the hand held device. In this embodiment the specialized mouthpiece can be enclosed within and/or presented for use by a mouthpiece cover 209 (FIG. 31) and/or the left cover 233 and the right cover 234 (FIGS. 38 and 40) can be configured to be manually and/or mechanically opened and closed.

The liquid/hydration specialized mouthpiece can be used without pressure switch 252A, power signal unit 252, and power source 139.

The liquid/hydration specialized mouthpiece can be used on any liquid container cap. Flow tubes would travel down from the liquid delivery chamber 251 through the liquid container cap and into the connected liquid container. The liquid container cap and/or liquid container must have an air filter check valve and/or flap inlet allowing the user to orally draw up liquid through the liquid/hydration specialized mouthpiece from the corresponding connected liquid container. Further, the liquid/hydration specialized mouthpiece can be fitted with covers that are pushed to the side or are removable and/or replaceable.

The specialized liquid/hydration mouthpiece shown in FIGS. 38-44 has function control pressure switches and/or a signal indicator lights 237A facilitating function control by the user. Function control is also enabled at the base unit.

To present the specialized liquid/hydration mouthpiece shown in FIGS. 38-44, the left push bar 235 and right push bar 236 are pressed in. A spring plunger 241 connected to left push bar 235 travels within spring casing 242 and condenses a spring 243 to release the cover. Toothed push rod 240 rotates gear 239 which in turn rotates right gear 239A. The toothed push rod 240 is connected to the right push bar 236. The right gear 239A rotates the right cover gear 234A and the connected right cover 234 opens. The rotation of the right gear 239A rotates the left gear 239B which rotates the left cover gear 233A and connected left cover 233 open revealing the liquid/hydration mouthpiece cap 212 presented for use.

The user presses on the mouthpiece cap 212 (FIG. 51), to receive pumped liquid through the mouthpiece cap 212, or manually by drawing up liquid through the mouthpiece cap 212 from a base unit.

Spring plunger 241 is a cylinder shaped component connected to the interior of the left push bar 235. The spring casing 242 is a hollow cylinder shaped component connected to the interior of right push bar 236, spring 243 resides within spring casing 242, placing pressure on the end of spring plunger 241.

When mouthpiece cap 212 and left push bar 235 and right push bar 236 are released condensed spring 243 pushes spring plunger 241 out so that left push bar 235 and right push bar 236 and the corresponding left cover 233 and right cover 234 return to their original closed position. The right cover 234 and left cover 233 rotate open and closed in unison. Left cover gear 233A (FIG. 44) is connected to the left cover 233 and rotation axel 254A. Rotation axel 254A is connected to left cover 233 and rotates within the side of the spring enclosure 250A. Gear 239, right gear 239A and left gear 239B rotate on axles, are connected to spring enclosure 250A and extensions connected to the spring enclosure 250A.

In a particularly preferred embodiment, the liquid/hydration specialized mouthpiece has a lockout pin flange 245C which stops left cover 233 and right cover 234 from closing when the mouthpiece cap 212 is pressed down and left push bar 235 and right push bar 236 are released. Releasing pressure on the mouthpiece cap 212 accompanied by releasing pressure on the left push bar 235 and the right push bar 236 allows the left cover 233 and the right cover 234 to close sealing and securing the mouthpiece cap 212 from outside contamination. The lock out pin guide slot 208C (FIG. 42) is an opening through spring enclosure 250A allowing the lock out pin flange 245C protruding through spring enclosure 250A (FIG. 44), and rest between and above left gear 239B and right gear 239A.

In a preferred embodiment, the left push bar 235 has an attachment slot 235A (FIG. 43) and can have an attachment connector 280 (FIGS. 66 and 67) which is replicated in an attachment slot within push bar 236 (not shown). A variety of shape and/or sizes of attachments can be added to the attachment connector to address the specific needs of a user like, for example, an arthritic user.

FIG. 68 shows another embodiment of a means to open and close the covers over mouthpiece cap 212. Covers 276 and 277 move when the user depresses the push bar 275. The push bar is connected to a spring tensioned gear which in turn rotates other gears to open the covers.

The specialized liquid/hydration mouthpiece within the liquid/hydration hand device FIG. 38 of the subject invention can be replaced by other suitable mouthpieces which include, but are not limited to, a simple tube, or a CAMELBAK bite wing.

One skilled in the art would realize a number methods of manually and/or mechanically opening a cover and/or covers, revealing a tube and/or a liquid delivery apparatus, as well as realize a number methods of manually and/or mechanically closing a cover and/or covers, and enclosing a tube and/or a liquid delivery apparatus within.

A system that allows the unit to be purged with air through the liquid flow tubes and corresponding components would enhance the removal/replacement of component parts. FIG. 69 shows a preferred embodiment of an air purging system. The system has a flow chamber unit 158 and a pump 166 with air filter 129 to purge air through selected flow tubes. Selected flow tubes can include, for example, liquid/hydration flow tube 143A, liquid/hydration flow tube 144A and sanitizing/neutralizing flow tube 134. Check valves/flaps 159 prevent fouling of the system.

Another preferred embodiment of a purging system is shown in FIG. 70. The system comprises a flow chamber unit 158, a pump 166 with air filter 129 to pump purging air from a selected flow tube through one liquid flow tube 162. FIG. 71 shows another preferred embodiment which is a simplified air purging system having a pump 166 with air filter 129 and check valves/flaps 159 for pushing purging air through one liquid flow tube 162.

The air purging system shown in FIGS. 69 and 70 have a rotating cylinder as part of their flow chamber unit 158. Flow in the rotating cylinders can be controlled by rotating tab 281 within the rotating tab plate 282. The rotation of the rotating tabs 281 corresponds to rotation of rotating flow cylinder 283, and corresponding rotating flow cylinder channel 284 allowing flow through the flow channel 285 (FIG. 78). The rotating flow cylinders 283 and corresponding components can have seals, for example, O-rings. One skilled in the art would realize a number of methods to manually and/or mechanically rotate a rotating tabs 281.

An alternative design for control of air from the flow chamber unit is shown in FIGS. 80-84. This design uses a push flow cylinder. The flow chamber unit 158 has push plungers 286. Push cylinder 287 within the flow chamber unit 158 resides between spring 291 and push plunger 286. A guide pin 289 travels up from the base of the flow chamber unit 158 and enters into a guide pin channel 290 within the push cylinder 287.

FIG. 82 is a view through push cylinder channel 288. FIGS. 81 and 82 show the system in a non-air flow mode. FIG. 84 shows the system in an in-flow air flow mode. The push plunger 286 pushes down the push cylinder 287, the push cylinder channel 288 aligns with flow channel 285 allowing air and/or liquid flow through flow chamber unit 158. Releasing of the push plunger 286 allows the spring 291 to return the push cylinder 287 to a non-flow mode. An air inlet/outlet channel 292 with an air filter equalizes air pressure within the area below the push cylinder 287, as the push cylinder 287 travels up and down.

Purging air through the liquid system allows liquid-free removal and replacement of component parts. Selected components can be removed and replaced in the device of the subject invention. The removal/replacement of selected components, while reusing components of a more costly nature would financially benefit the user and allow use of the device by multiple users. Further purging air through the liquid system allows displacement of fluids and replacement of those fluids with another choice for hydration.

The removal and/or replacement of the components shown in FIG. 36 is accomplished by rotation of connector knob 138 disconnecting the change out base plate 148 from the change out base 147 (FIG. 34). The connector knob 138 is threaded into the threaded connector channel 138A located in the change out base plate 148. The change out base 147 is hidden behind the change out base plate 148.

Suction tube 103 is removed from the contaminant collection container 136. In a preferred embodiment suction tube 103 removal includes removal from within a peristaltic pump 116 (FIG. 33). The separator connection 128 provides a point of separation.

In preferred embodiments, components of the hand held device are removable. Removal of grips etc. would allow replacement with device shown in FIGS. 64 and 65. FIG. 64 provides flexibility of rotation of the hand held device with function control. FIG. 65 shows a ringed grip to enhance use by those who are physically challenged.

The containment unit 153 can be removed from the hand held device. Removal of components within the containment unit 153 allows for the cleaning and/or replacement of the sliding suction tube 154. Containment cover 163 can be replaced with a variety of shapes and sizes of attachments made for physically challenged users, for example, the cover shown in FIG. 63 has a thumb ring.

FIG. 34 shows the flow tubes 126A, 134, 141A, 143A and 144A correspond to the liquid outlets 150, 149, 263, 143A and 144A, and connect into inlets located (not shown) on the rear facing side of FIG. 35. The outlet/inlet connections have O-ring's and check valves and/or flaps. Liquid level sensor 135 corresponds to a connection into 135A, the purging tube 145 connects into 145A, the heat wire 160 connects into 161. The heat wire 160 allows warming of the base unit, the hand held device and components between the base unit and the hand held device.

Power/signal source wires 139 travels to a hand held device. Power/signal source wire 139A (FIG. 9) connects into the power/signal source wire connector 139B (FIG. 18), located within the power/signal control unit 112A (FIG. 15), transferring power and/or signals between the base units and connected hand held devices. In an exemplified embodiment, transfer of signals would be a remote control 123 (FIG. 33) communicating with a remote control located within the corresponding hand held device.

The subject invention is a suctioning device and/or a liquid-hydration delivery device, which is adaptable to perform a number of oral and/or non-oral, suction and/or liquid-hydration delivery use scenarios. The combination of separately designed base units, hand held devices, corresponding components encompass multiple design functionality requirements to enable use of a separate suction device, a separate liquid-hydration delivery device, or a combination of a suction device and liquid-hydration delivery device.

The suction device of the subject invention, enhanced with the liquid-hydration delivery device provides a user a clean, sanitized means to tend to the user's condition. Whether suctioning toxic dye from a plate in a laboratory setting, rinsing and removing drainage from a wisdom tooth extraction, or providing hydration during uninterrupted activity, the subject device provides clean suction and/or liquid-hydration delivery, with safe, easy disposal of waste.

It is understood that the foregoing examples are merely illustrative of the present invention. Certain modifications of the articles and/or methods may be made and still achieve the objectives of the invention. Such modifications are contemplated as within the scope of the claimed invention.

The invention claimed is:
1. A liquid hydration delivery device comprising:
at least one delivery tube to deliver at least one liquid from at least one container, the at least one delivery tube having one end in fluid communication with the at least one container and another end;

a mouthpiece in fluid communication with the another end of the delivery tube, the mouthpiece having an opening;

a mouthpiece cap, the mouthpiece cap comprising a honeycomb, the honeycomb having a non-perforated base plate;

wherein the mouthpiece cap is spring biased so the non-perforated base plate of the honeycomb seals the opening of the mouthpiece; and wherein said at least one liquid is dispensed through the mouthpiece cap when the mouthpiece cap is pressed down onto the mouthpiece orally by a user.

2. The liquid hydration delivery device of claim 1, further comprising a cover.

3. The liquid hydration delivery device of claim 2, wherein said cover comprises two pieces that rotate to separate along a centerline.

4. The liquid hydration delivery device of claim 3, wherein said cover comprises two pieces that rotate to separate along a centerline by movement of gears.

5. The liquid hydration delivery device of claim 1, further comprising a pump to move liquid from the at least one container through the at least one liquid delivery tube.

6. The liquid hydration delivery device of claim 1, wherein said container is pressurized.

7. The liquid hydration delivery device of claim 1, wherein said delivery tube further comprises a liquid delivery chamber and a purging tube to clear the liquid delivery chamber of said at least one liquid.

8. A liquid hydration delivery device comprising at least one delivery tube to deliver at least one liquid from at least one container, the delivery tube comprising a mouthpiece, wherein the mouthpiece permits flow of said at least one liquid when a portion of the mouthpiece is depressed, the mouthpiece enclosed in a two piece cover that rotates to separate along a centerline.

9. The liquid hydration delivery device of claim 8, wherein said two piece cover that rotates to separate along said centerline by movement of gears.

* * * * *